United States Patent [19]

Risby et al.

[11] 4,075,475
[45] Feb. 21, 1978

[54] PROGRAMMED THERMAL DEGRADATION-MASS SPECTROMETRY ANALYSIS METHOD FACILITATING IDENTIFICATION OF A BIOLOGICAL SPECIMEN

[75] Inventors: Terence H. Risby, State College, Pa.; Alfred L. Yergey, III, Columbia, Md.

[73] Assignee: Chemetron Corporation, Chicago, Ill.

[21] Appl. No.: 682,781

[22] Filed: May 3, 1976

[51] Int. Cl.² .................. B01D 59/54; H01J 39/34
[52] U.S. Cl. .............................. 250/282; 250/288
[58] Field of Search ............ 250/281, 282, 288, 252, 250/423, 425

[56] References Cited
PUBLICATIONS

"Nonisothermal Kinetics Studies of the Hydrodesulfurization of Coal", Yergey et al., I&EC Process Design & Development, vol. 13, pp. 223-240, July 1974.
"Thermal Analysis-Mass Spectrometer Computer System and its Application to the Evolved Gas Analysis of Green River Shale & Lunar Soil Samples" Gibson, 23 Confer. on Anal. Chem. and Appl. Spectroscopy, 1972, pp. 243-255.

*Primary Examiner*—Bruce C. Anderson
*Attorney, Agent, or Firm*—Cushman, Darby & Cushman

[57] ABSTRACT

A method facilitating the rapid and objective classification and/or identification of an unknown biological specimen is disclosed. A physical sample of the specimen is controllably heated in accordance with a predetermined nonisothermal time dependent function causing the sample to undergo controlled thermal degradation and give off a characteristic time dependent sequence or evolution pattern of gaseous degradation components (molecular fragments). This sequence of gaseous degradation components is then directly passed into an ionization source and ionized to provide a respectively corresponding time dependent sequence of characteristic ions. These ions are then analyzed in a mass spectrometer and measured data is recorded representing the respective quantities of ions having particular masses being produced as a function of time or temperature. This recorded data for an unknown biological specimen is then correlated with analogous time or temperature dependent data earlier recorded for known biological specimen thereby facilitating the classification and/or identification of the unknown biological specimen. The method may be used to facilitate the classification and identification of many different types of biological specimen such as, for example, biological organisms (e.g., bacteria, yeast, molds, fungi, viruses and unicellular animals) and/or biological tissues (e.g., lymphocytes, leukocytes, phagocytes, erythrocytes and platelets).

56 Claims, 46 Drawing Figures

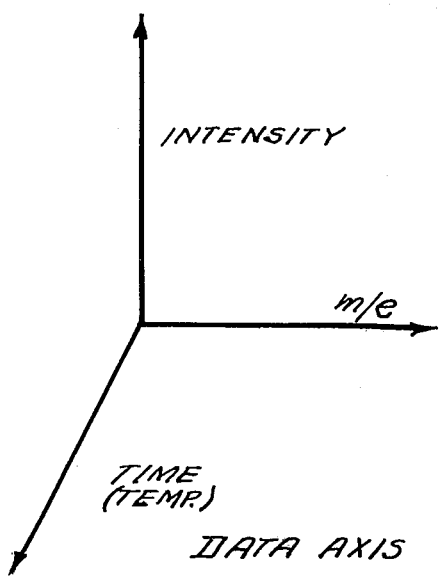
Fig. 1c — DATA AXIS
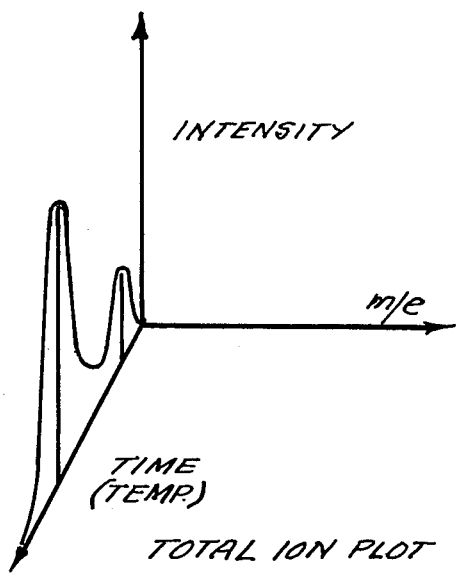
Fig. 1D — TOTAL ION PLOT
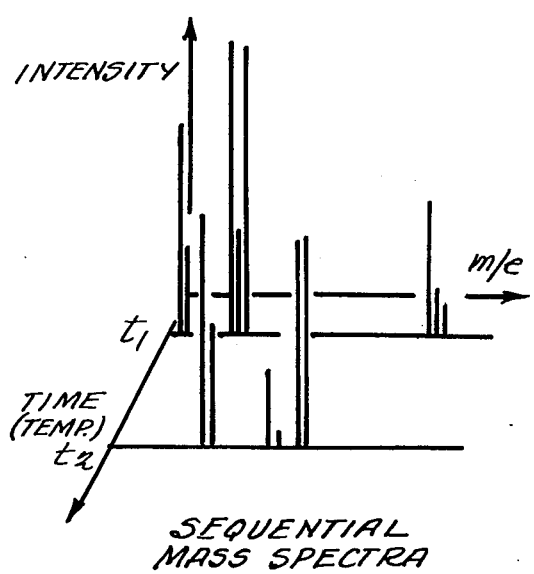
Fig. 1E — SEQUENTIAL MASS SPECTRA
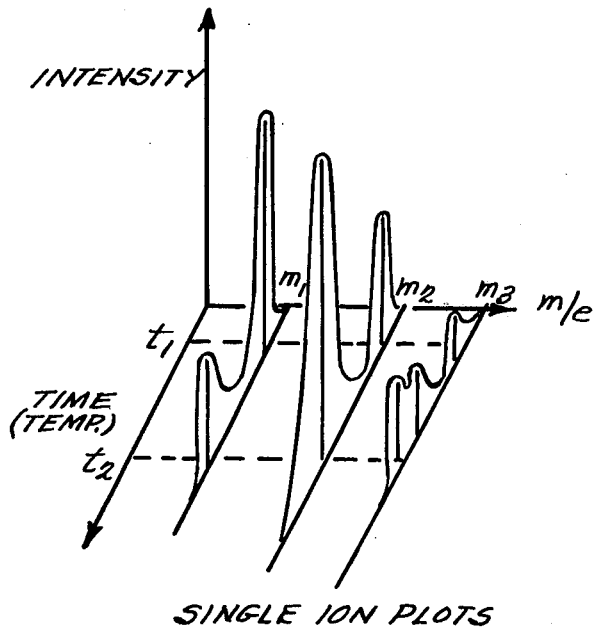
Fig. 1F — SINGLE ION PLOTS

ION MASS/ELECTRON RATIO
PSEUDOMONAS PUTIDA ATCC #15073
BACTERIA #2

BACTERIA #3
PSEUDOMONAS FLUORESCENS

ION MASS/ELECTRON RATIO
PSEUDOMONAS PUTIDA ATCC #15073
BACTERIA #3

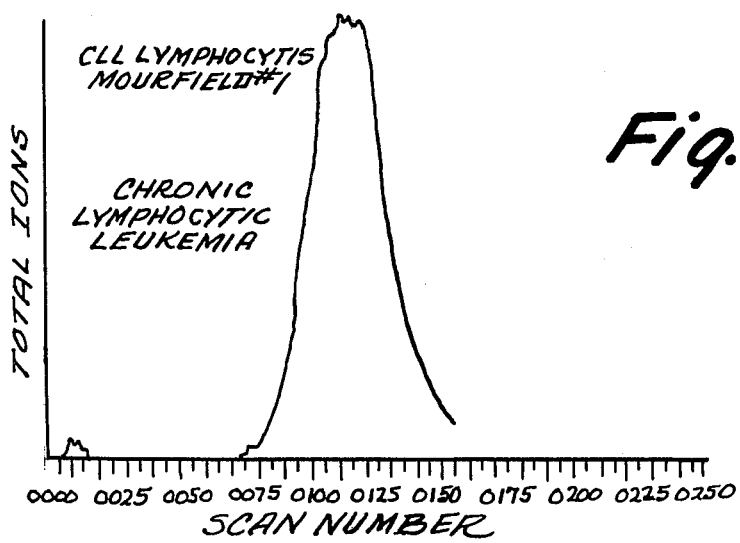
Fig. 40
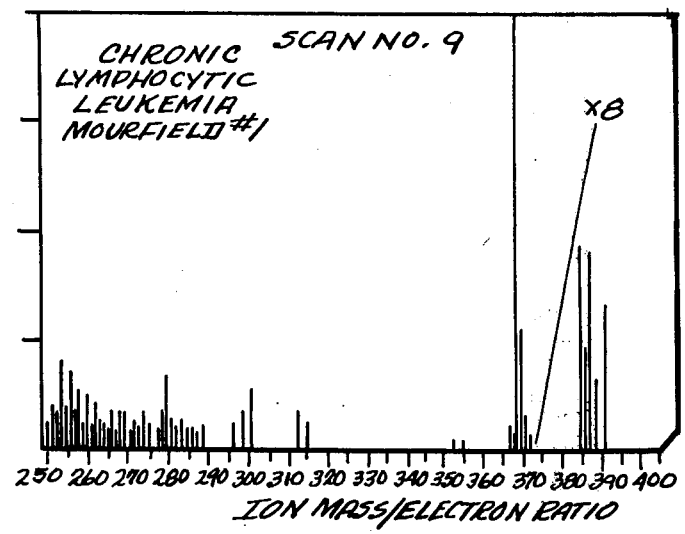
Fig. 41
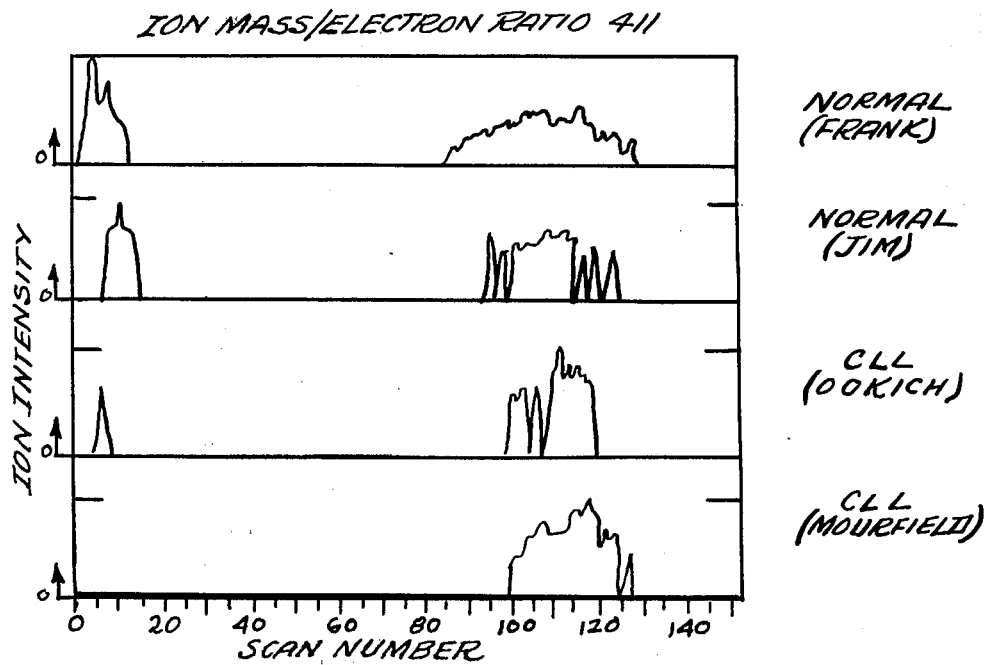

PROGRAMMED THERMAL DEGRADATION-MASS SPECTROMETRY ANALYSIS METHOD FACILITATING IDENTIFICATION OF A BIOLOGICAL SPECIMEN

This invention generally relates to a method which facilitates the rapid and objective classification and/or identification of an unknown biological specimen. The method involves programmed thermal degradation of a biological specimen followed directly by mass spectrometry analysis of the resulting temporal sequence of evolved gaseous degradation components and the monitoring of relative ion intensities produced for particular ion masses as a function of time or temperature. The method is believed to be generally advantageous for assistance in classifying and/or identifying many different types of biological specimen representative of living biological organisms and/or tissues. For example, such biological organisms may include bacteria, yeasts, molds, fungi, viruses and/or unicellular animals. Typical biological tissues would include lymphocytes, leukocytes, phagocytes, erythrocytes and/or platelets. Particular recorded data according to this invention for certain bacteria and certain lymphocytes is presented in the following description of the invention.

The process uses evolution patterns of molecular fragments generated during the well controlled thermal degradation of biological specimen. These evolution patterns are used as the identifying characteristics for identifying and/or classifying the specimen. A salient feature of this process is that programmed increase in the temperature of the specimen produced temporal separation of the discrete decompositions occurring in the specimen cells. The degradation is preferably carried out in the source volume of a chemical ionization mass spectrometer which is used to monitor evolving molecular fragments.

The identification of biological specimen such as bacterial organisms is important for a set of human problems, which range from maximizing food production to controlling and preventing certain diseases. Solutions to these problems is approached from a wide variety of standpoints which depend upon the nature of the organisms to be identified, the time available for the task and the degree of identification required. A frequently encountered problem, and the one ultimately addressed by this invention is the identification of strains of pathogenic bacterial species. The need for strain identity within a particular species is due to behavioral differences, which occur at that level, e.g., antibiotic resistance of some strains and not others. The fact that such organisms may be human pathogens creates the need for the identification to be carried out as rapidly as possible. Since this invention will be applicable to a wide variety of biological systems, it should become a major new medical diagnostic tool. The inherent rapidity of analysis by this technique may provide physicians information to speed prescription of therapeutic measures.

As will be appreciated, the problem of classifying and/or identifying a given biological specimen into a particular family, genus, species and/or race (analogous to sub-species, bio-type and/or sero-type) is a long standing problem. Currently, the actual classification and/or identification of biological specimen involve techniques which are based largely on morphlogical, biochemical, chemical and/or serological tests and objectivity is often lacking in these techniques. Furthermore, these techniques are often excessively time consuming. Since the classification and/or identification of a given biological specimen is often directly related to a human health problem, there is a considerable history of past effort to improve the objectivity and/or speed of such techniques. However, the complexity of biological systems even in the static state and the difficulty generally expected by those in the art for obtaining meaningful measurements of physical and chemical properties for complex biological systems has been an effective obstacle in the past to the development of truly objective and rapid identification and/or classification techniques.

Several different instrumental approaches have been applied to the problem of bacteria identification. These methods fall into two broad classes—calorimetry and pyrolysis.

Calorimetric methods are split into two areas that are quite distinct. The first area is micro-calorimetric techniques, and the second is thermogravimetric methods. Microcalorimetry is the monitoring of heat evolved during the growth process. Bacterial organisms emit heat during growth in the range of 40–60 $\mu$ cal/sec in a characteristic fashion. The method has been applied to more than 200 organisms representing 47 species or types from 24 genera. Identification of organisms by this method depends upon the shape of the heat evolution curve. The disadvantage to the method is that occasionally, unrelated organisms produce similar traces that differ only in amplitude.

Thermogravimetric (TGA) and differential thermal analysis (DTA) methods have been applied to bacterial identification problems to only a limited degree. According to at least one published account, the reasons for the lack of DTA studies on organic systems such as bacteria is the overwhelming complexity of biological materials, and the difficulty others in the past have expected in obtaining meaningful results and of establishing correlations between thermal characteristics and other physical and chemical properties.

It is in the area of pyrolysis-gas chromatograph (py-GC) and pyrolysis-gas chromatograph/mass spectrometry (py-GC/MS) that instrumental techniques have shown most promise. The applicability of a mass spectrometer to analysis of pyrolysis products by sampling the total mixture resulting from the pyrolysis of complex materials has been shown elsewhere. It has also been shown that GC analysis of the pyrolysis products of bacteria can be used to detect subspecies differences among various organisms. The method has, for example, been applied to differentiation of Clostridium botulinum types and the differentiation of several species of fungi.

Use of a mass spectrometer to determine the identity of the compounds eluting from a GC has in this manner added information previously unattainable in pyrolytic identifications of bacteria. Isothermal pyrolysis, including Curie point pyrolysis, followed by mass analysis has also been used by a number of investigators for characterization purposes.

Briefly reviewing, earlier experimental exploration of more objective instrumental techniques by others included the well known DTA approach. This technique essentially involves the sintering of a sample within a block located within a furnace. The resulting temperature changes in the biological sample are plotted as a function of furnace temperature to provide temperature curves which are in some ways characteristic of the sample material. However, this earlier suggestion has apparently never been actually used as a practical identification and/or classification scheme. One possible reason for this failure is the probable lack of sufficient objective data from a DTA technique, per se, to practically and objectively effect classification and/or identification within the very large universe of biological specimen known to exist.

Another earlier approach to the problem of increasing the objectivity and/or speed of classification and/or identification of biological specimen involves the isothermal pyrolysis of a biological specimen followed by gas liquid chromatography. Some of these earlier workers in the field have also suggested the employment of a mass spectrometric analysis for the gaseous products sequentially evolving from the gas-liquid chromatograph. Unfortunately, however, a great amount of potentially useful information is necessarily lost by these techniques in that the pyrolysis involved is a very quick isothermal process which effectively eliminates the information which might otherwise be obtained from a characteristic time dependent evolution of thermal degradation components produced by a more gradual programmed thermal degradation spread over a longer time interval. Furthermore, the employment of gas/liquid chromatography completely masks any information which might have been provided by the original time dependent production of thermal degradation components in the original sample since the time dependence of evolutions from the chromatograph are a function of the chromatograph rather than the original pyrolysis or thermal degradation process. In effect, the employment of a chromatograph in such techniques totally eliminates whatever time dependent information might have been originally available in the pyrolysis or thermal degradation process of the biological specimen. In any event, such prior art attempts at classification and/or identification of biological specimen using processes involving a chromatograph have never been employed on a practical commercial scale.

Another prior approach towards improving the process of identifying and/or classifying biological specimen has involved isothermal pyrolysis of such a specimen followed directly by mass spectrographic analysis of the products of such pyrolysis. However, such prior isothermal pyrolysis processes inevitably fail to provide the wealth of potentially available information that may be obtained from the time dependent production of degradation components produced by a more gradual programmed thermal degradation of the specimen. Furthermore, any possible time dependent information involved in such prior approaches has been effectively masked or thrown away in that only the mass spectrum occurring during a peak output of the pyrolysis process was observed and/or recorded for usage.

Now, however, we have discovered that a practical, very rapid and substantially more objective classification and/or identification of biological specimen may be effected by controllably heating a biological specimen in accordance with a predetermined non-isothermal time dependent function so as to provide a characteristic time dependent sequence of gaseous degradation components followed by the direct ionization and mass spectrometric analysis of such components together with the recording of measured data representing the respective quantities of ions having particular masses being produced as a function of time or temperature. In this manner, the time dependent information either not produced or ignored in the earlier approaches to this problem as discussed above is purposefully produced and carefully recorded for usage.

In carrying out the method of this invention, a sample of biological specimen having known and predetermined identity or classification will first be provided and controllably heated in accordance with a predetermined nonisothermal time dependent function thereby providing a characteristic time dependent sequence of gaseous degradation components (molecular fragments) related uniquely to the known biological specimen. This characteristic time dependent sequence of components from the known biological specimen are then directly passed within a mass spectrometer ion source and ionized to provide a respectively corresponding characteristic time dependent sequence of ions. This time dependent sequence of ions is then analyzed and detected within the mass spectrometer and a set of measured data is recorded representing the respective quantitites of ions having particular masses as a function of time or temperature. Preferably, these steps are carried out for a large number of biological specimen each having known predetermined identity or classification so as to provide a family or library of sets of measured data each uniquely corresponding to a biological specimen having known predetermined identity. Thereafter, the same process steps are repeated at least once for a sample of biological specimen having unknown identity or classification. The measured data set resulting from this process for the unknown is then compared or correlated to the earlier recorded sets of measured data for the known. Thus, the process of this invention facilitates the classification and/or identification of the unknown biological specimen. The actual comparison and/or cross correlation of the various sets of measured data is preferably carried out by machine in a conventional data processor conventionally programmed to perform comparison and/or cross correlation algorithms which are, per se, known in the art.

The process of this invention preferably utilizes a linear temperature increase during the controllable heating of the sample since such a linear function is easily realized and easily reproducible.

If the particular family, genus, species and race of a provided biological specimen has earlier been analyzed and the resulting data stored in the library of data representing known biological specimen, then the comparison or cross correlation of the corresponding set of data resulting from the process of this invention with the earlier recorded respectively corresponding set of recorded data will be substantially complete and corresponding substantially complete identification of the unknown specimen may be provided down to the lowest taxonomical order. On the other hand, if the prior recorded library of sets of recorded data does not include data substantially completely correlated with the data resulting from the unkown specimen, there may nevertheless be earlier recorded data from specimen in the same family or genus, etc., thus permitting the classification of the unknown biological specimen into one or more of the higher taxonomic orders even though complete identification as to all of the lower taxonomic orders may not be possible.

Our invention also includes the discovery that the molecular fragments or components produced by the programmed thermal degradation process should preferably be ionized in an ionizing process which does not diminish the mass of the molecular fragments or components by more than one mass number. The preferred form of such an ionizing process for use in this invention is the well known chemical ionization (CI) process now widely recognized in the art of mass spectrometry as a result of its description, inter alia, in U. S. Pat. No. 3,555,272 issued Jan. 12, 1971. For example, it has been discovered that use of other ionization techniques such as conventional electron impact (EI) ionization, which often severely fragments the parent ions produced by the thermal degradation process, results in the loss of significant identifying data and/or in the confusion of analysis results and poor reproducibility. Accordingly, ionization processes which fragmentize to effect ionization materially lessen the ability of this invention to distinguish between a large universe of biological specimen. Accordingly, an ionization process which does not significantly diminish the mass of the molecular fragments during ionization (e.g., chemical ionization, electron capture modes of EI, field ionization, etc.) is preferred for use with this invention.

Furthermore, when a CI ion source is utilized, as in the preferred embodiment of this invention, the necessary reagent gas (water vapor, methane and other typical reagent gases may be used as will be appreciated) is passed directly over the thermally degrading sample into a chemical ionization zone within the chemical ionization source whereby the components of thermal degradation are swept along by the reagent gas directly away from the site of the degrading sample to the ionization zone thus insuring that the same characteristic time dependent sequence of evolving components is directly provided to the ionization zone.

The programmed thermal degradation of the biological speciment according to this invention is preferably carried out directly within the chemical or other ionization source by the placement of the sample onto a heated solids probe which is inserted through a vacuum seal into the ionization source. Preferably, the heated solids probe includes an electrical heater for heating the sample as well as a temperature sensor which provides an electrical indication of the probe temperature. The temperature sensor electrical output is utilized to control the supply of electrical energy to the heater so as to cause the temperature of the sample to increase in accordance with the desired predetermined non-isothermal time dependent function.

In performing the method of this invention, it has also been discovered that it is sometimes helpful to detect the total ion current flowing within the mass spectrometer (from all ion masses) and to record further measured data showing the intensity of such total ion current as a function of time or temperature. Preferably, in this embodiment of the invention, this further recorded data is included with the other time dependent measured data and incorporated as a part of the sets of time dependent data which are to be utilized in comparison and/or cross correlation for classifying and/or identifying biological specimen.

In a still further embodiment of this invention, it has been discovered that it is sometimes helpful to also record the spectrum of ion masses occurring at different instants during the thermal degradation process. Such spectra may conveniently be utilized for identifying particular predetermined ion masses to monitor as a function of time or temperature according to the earlier stated embodiment of this invention. These spectra taken at different instants of time may also be included with the other measured data for use in the comparison and/or cross correlation of data to classify and/or identify biological specimen as earlier discussed.

After making this discovery, our research of scientific literature relating generally to DTA and/or TGA reveals that others in the past have analyzed non-biological specimen by employing DTA and/or TGA followed directly by mass spectrometric analysis of the evolution products of such TGA and/or DTA. However, even with respect to this analysis of non-biological specimen, and even where time dependent information (e.g., the relative intensity of a particular ion mass versus time) was recorded as measured data, the time dependent kinetics information was derived from traditional thermograms or other traditional TGA/DTA plots with the recorded mass spectrometric data being employed only to help interpret the traditional thermogram analyses, etc. In any event, these earlier analysis techniques for non-biological specimen are not involved with the classification and/or identification of the specimen into a particular family, genus, species, race, etc. Nor are they even involved with analysis of biological specimen. In fact, substantially all, if not all, such prior analyses presently known utilize mass spectrometers having conventional EI ion sources. As pointed out above, such EI ion sources are detrimental to the present invention. Thus these prior DTA, TGA and DTA/TGA-MS techniques as applied to non-biological specimen are not believed to be truly relevant to the present invention.

It is also known that coal degasification processes have been studied, in part, by non-isothermally degrading the coal and analyzing the kinetics of the coal degasification process by mass spectrographically analyzing the products of such non-isothermal degradation. Of course, such prior studies relate solely to an attempt to more accurately understand the kinetics of coal degasification and/or hydrodesulfurization of coal. There was no realization in these coal degasification studies that any aspect thereof might be useful in classification and/or identification of biological specimen.

Further advantages and objectives of this invention will be evident from a study of the following more detailed description of several exemplary embodiments of this invention in conjunction with the accompanying drawings, of which:

FIGs. 1C, 1D, 1E and 1F are graphical depictions of the types of recorded data which may result from this invention and of the utilization of such data to facilitate the classification and/or identification of biological specimen;

FIGS. 34 – 41 are plots of total ion intensity versus time or temperature and a spectrum of ion mass taken at a time corresponding to the leading edge of the first peak of total ion current for both normal and abnormal lymphocytes; and FIG. 42 is a plot of relative ion intensity versus time or temperature for the specific ion mass of 411 for both the normal and abnormal lymphocytes giving rise to the data presented in FIGS. 34 – 41.

Figure 1A:
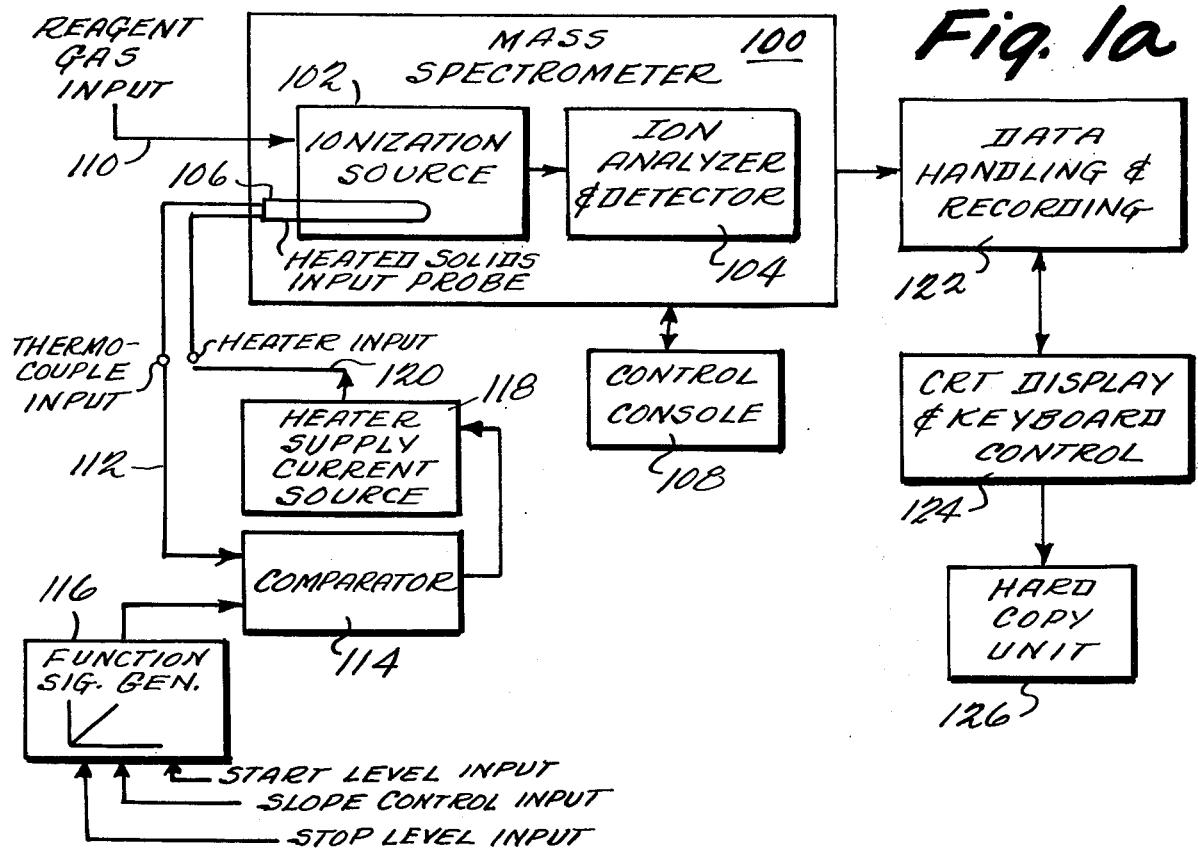
FIG. 1A is a schematic-block diagram of a typical arrangement of conventional apparatus which may be used in practicing this invention.

Referring first to FIG. 1A, apparatus is there shown in block diagram form of a type which may be conveniently used for practicing this invention. Of course, it will be understood that this particular arrangement of apparatus is only exemplary in nature and that other arrangements of conventional apparatus may also be employed. The apparatus shown in FIG. 1 includes a mass spectrometer 100 which has, internal thereto, an ionization source 102 and an ion analyzer and detector 104 as will be appreciated. In addition, in the preferred embodiment, the mass spectrometer ion source 102 includes a heated solids input probe 106 which probe 106 is adapted to heat a sample in the solid phase. Typically, an electrical heater will be incorporated with the probe as well as a thermocouple to monitor the probe temperature. The mass spectrometer 100 will also usually have a conventional control console 108 associated therewith as will be appreciated.

The mass spectrometer 100 is preferably of a type which does not significantly diminish the mass of parent ions during the ionization process carried forth within the ion source 102. In particular, the preferred form of the invention utilizes a chemical ionization ion source 102. However, other types of ionization are also available which do not significantly diminish the mass of parent ions. For example, an ionization process involving electron capture by impinging electrons having less than about 20 ev energy may be a suitable alternate type of ionization as may be field ionization, etc. A suitable conventional chemical ionization mass spectrometer for use with this invention would be the BIOSPECT chemical ionization mass spectrometer available from Scientific Research Instruments Corporation, Baltimore, Md.

As will be appreciated, CI mass spectrometers require a reagent gas and, in the preferred exemplary embodiment shown in FIG. 1A, a reagent gas input 110 is provided. This reagent gas may be methane, water vapor or other reagents as will be appreciated. In the BIOSPECT chemical ionization mass spectrometer, such reagent gas is directed internally of the ionization source 102 to pass directly over the tip of the heated solids probe 106 so as to sweep the molecular fragments being produced directly therefrom and into an ionization zone within the ion source 102.

In the preferred exemplary embodiment shown in FIG. 1A, the thermocouple output on line 112 from the heated solids probe 106, is presented as one input to a comparator 114. The other input to comparator 114 is provided by a function signal generator 116. In this manner, the actual solids probe temperature is compared with a predetermined time dependent function and any deviation therefrom results in an output from comparator 114 to the heater supply current source 118 resulting in an increased or decreased supply of electrical energy to the heater input line 120 as necessary to cause the actual temperature of the heated solids probe 106 to accurately track the predetermined time dependent function provided by the function signal generator 116. Although a variety of predetermined time dependent functions may be utilized successfully with this invention, the preferred exemplary embodiment utilizes a linear ramp function generator 116 since a linear ramp is relatively simple to generate and a linear increase in the temperature of the heated solids probe 106 is more easily reproducible. Typically, the function signal generator, such as a linear ramp generator, will be provided with conventional circuits for determining the ramp slope, the initial starting level of the ramp and a stopping level of the ramp as well as any necessary reset or restart circuitry, etc.

The electrical output signals from the mass spectrometer 100 are presented to and accepted by a conventional data handling and recording system 122 which is under the control of a conventional keyboard circuit unit 124 for recording selected data corresponding to the analyzed and detected ions in the mass spectrometer. Typically, the keyboard control unit 124 also has associated therewith a CRT (cathode ray tube) display unit and/or a hard copy unit 126. A suitable conventional data handling and recording system together with suitable keyboard control, display and/or copy facilities is commercially available from, for example, Systems Industries of Sunnyvale, California, as their System 150. Other suitable data handling and recording apparatus systems are presently available from Hewlett Packard and from the Kerns Group.

The conventional heated solids probe provided with the BIOSPECT mass spectrometer is provided with a tip having a cylindrical well sized for receiving a small cylinder of glass (1 cm. long by 4 mm. outside diameter) containing a solid sample in its core of approximately 6 microliters volume. While this conventional heated solids probe is quite suitable for use with this invention and has been successfully utilized therein, a modified slotted tip heated solids probe as shown in FIG. 1B is actually preferred at present for use with this invention.

Figure 1B:
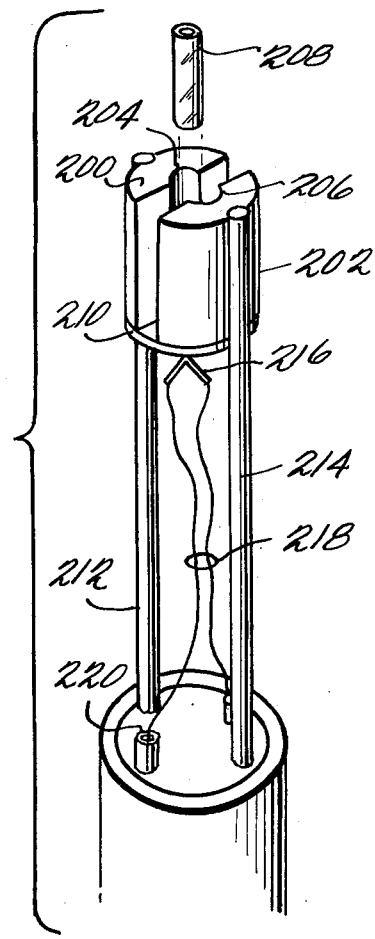
FIG. 1B is a perspective view of a special heated solids probe tip which is presently preferred for usage with this invention in the apparatus of FIG. 1A.
Figure 2:
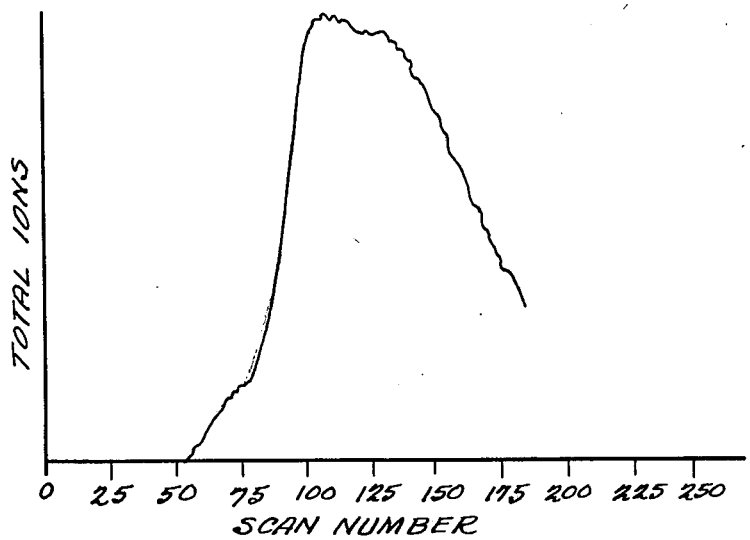
FIGS. 2 – 21 depict the total ion current versus time or temperature and one exemplary ion mass spectrum taken at a time corresponding to the leading edge portion of the total ion plot for each of ten particular types of bacteria in a process according to this invention.
Figure 3:
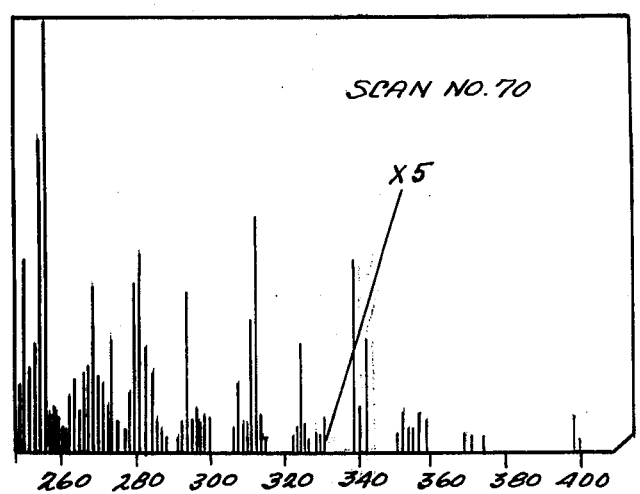
Figure 4:
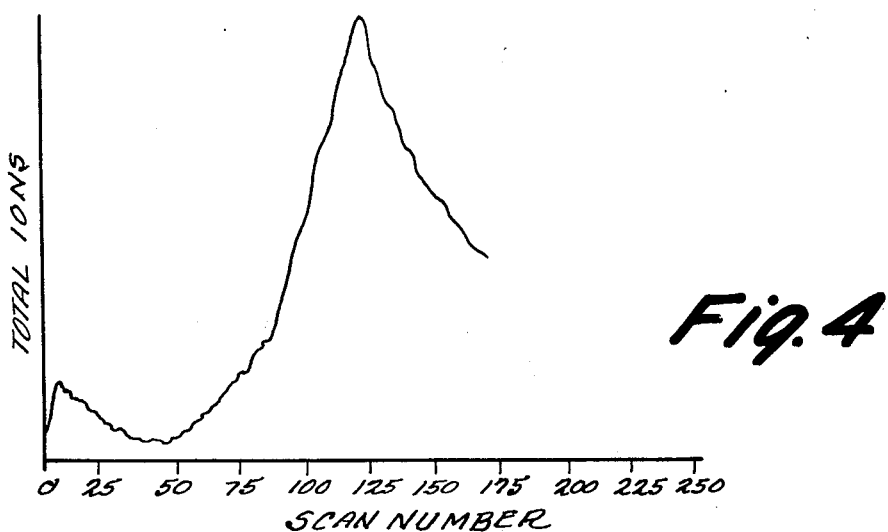
Figure 5:
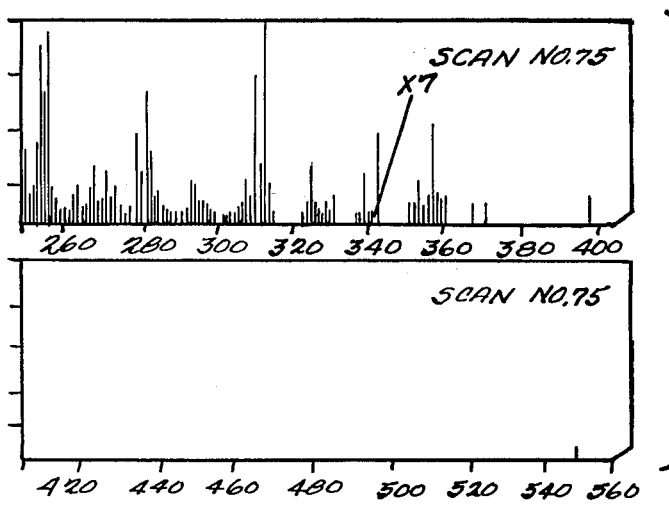
Figure 6:
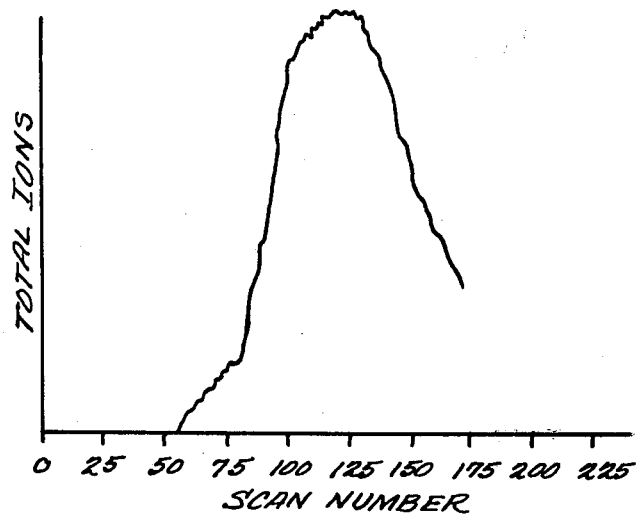
Figure 7:
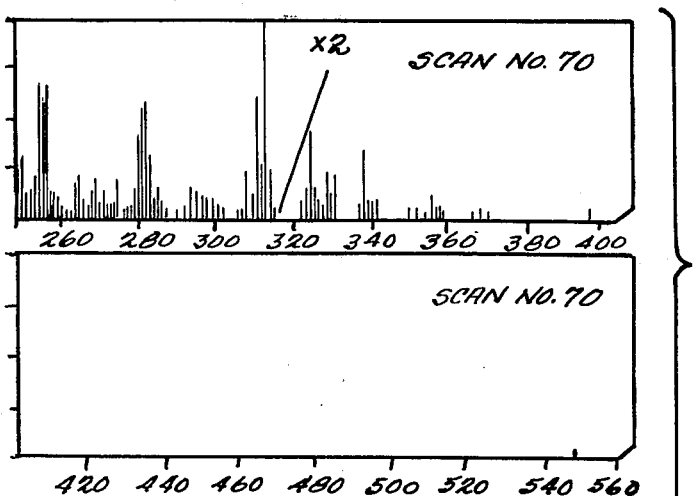
Figure 8:
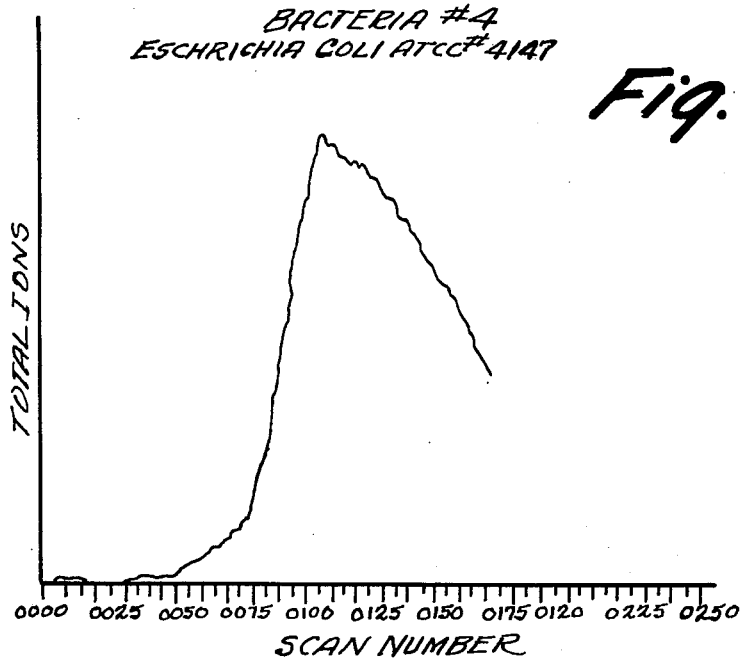
Figure 9:
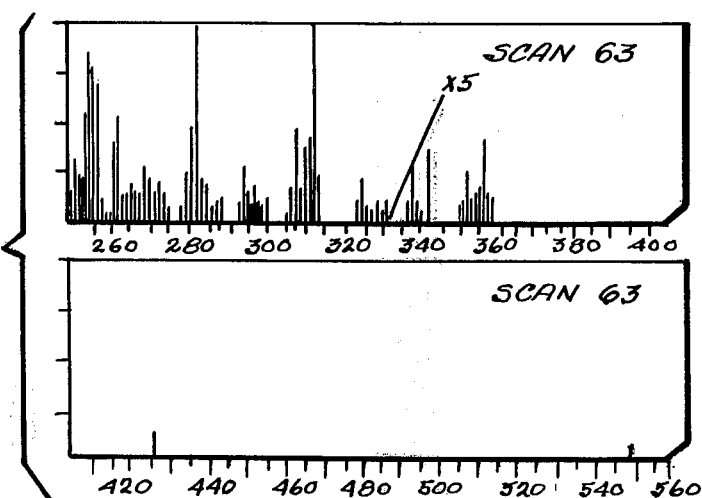
Figure 10:
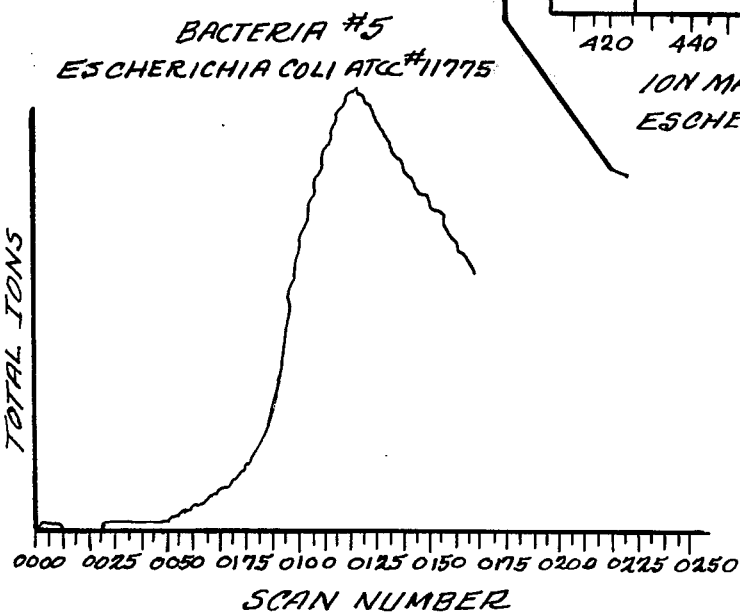
Figure 11:
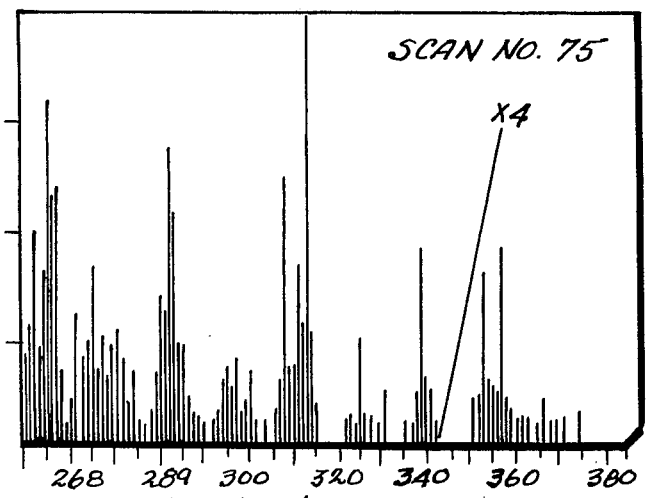
Figure 12:
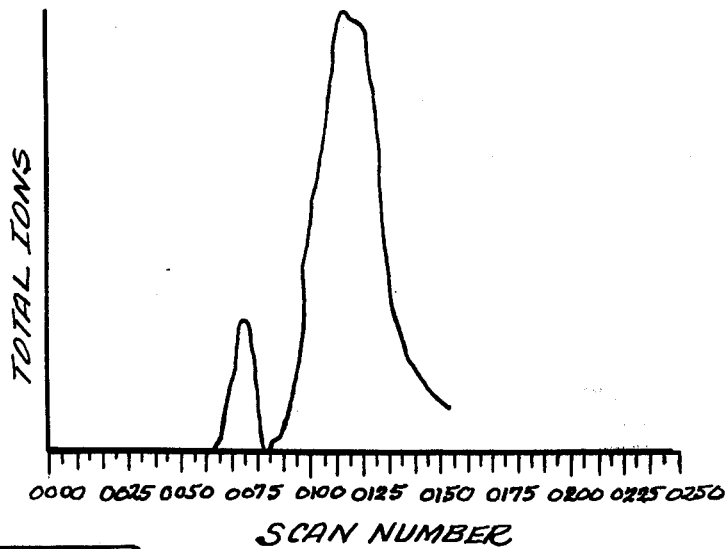
Figure 13:
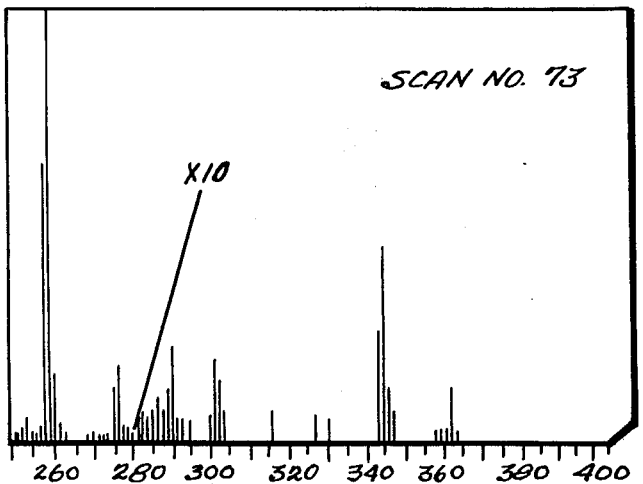
Figure 14:
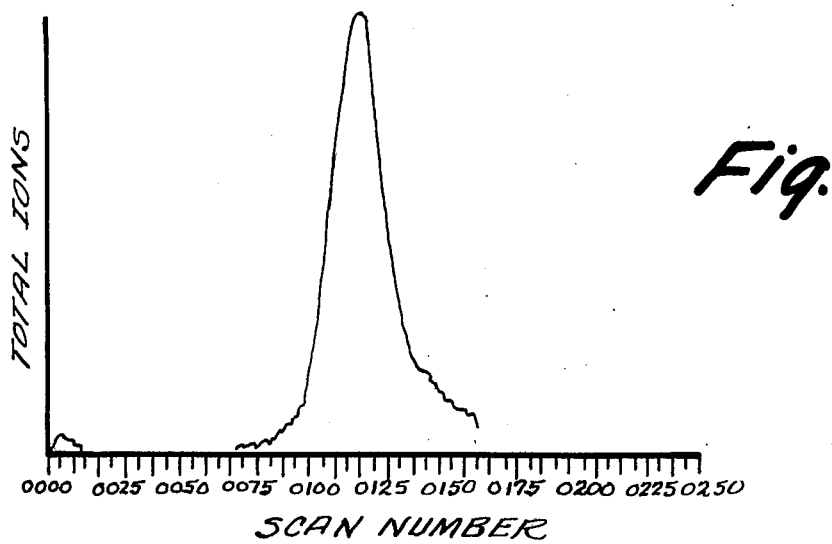
Figure 15:
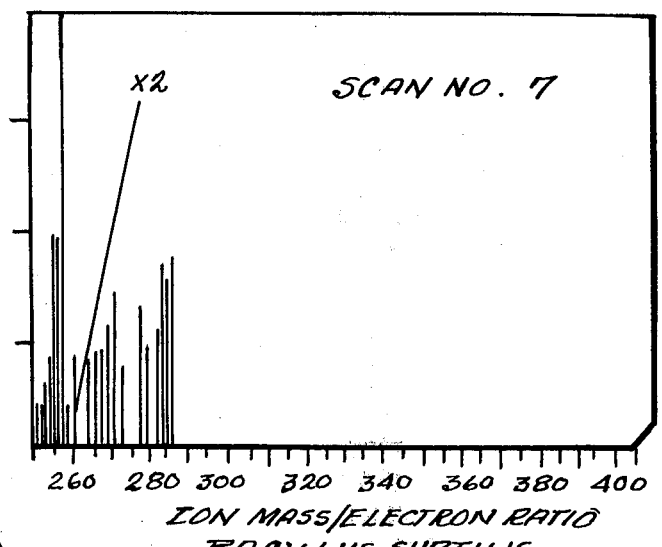
Figure 16:
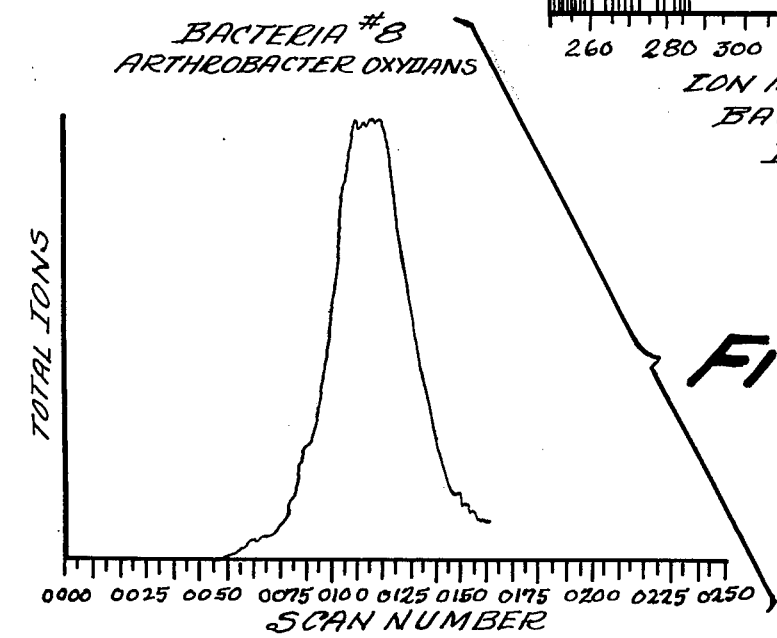
Figure 17:
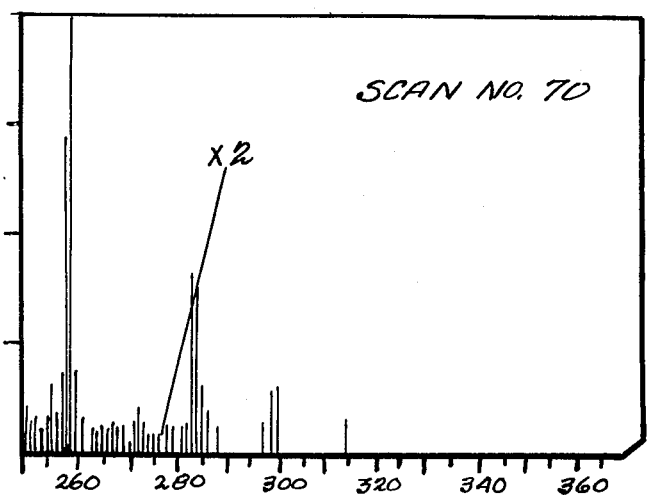
Figure 18:
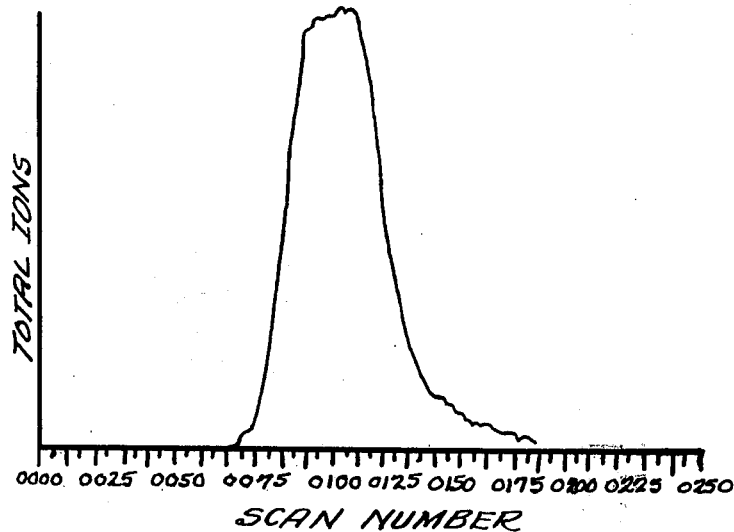
Figure 19:
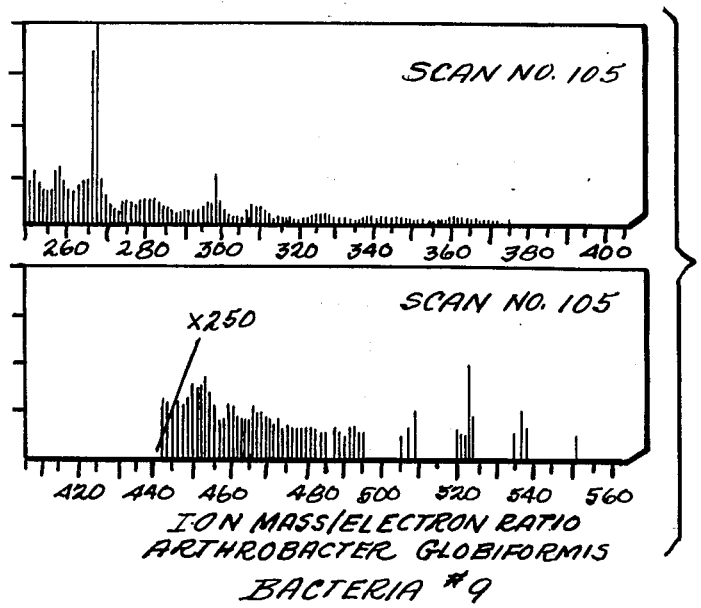
Figure 20:
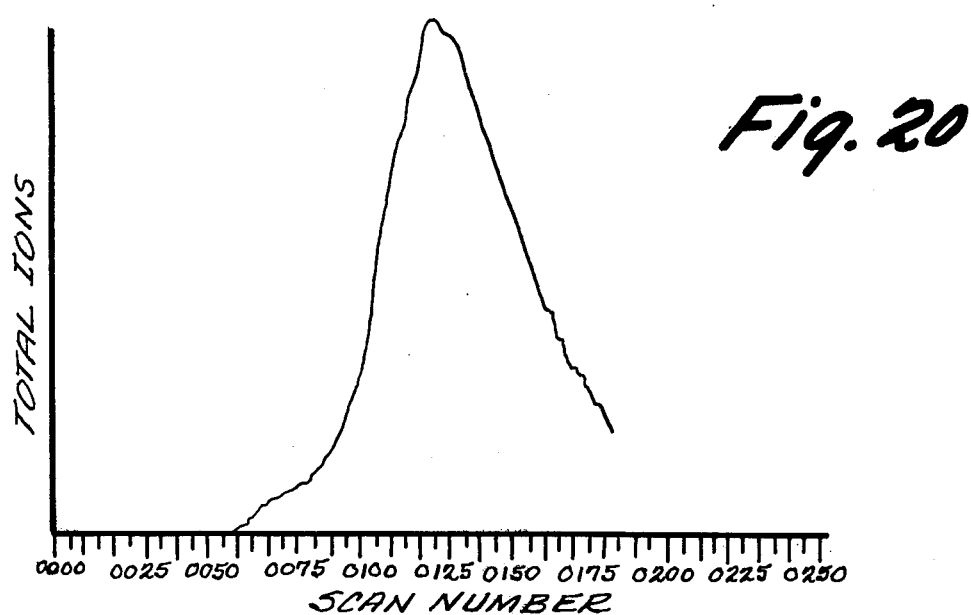
Figure 21:
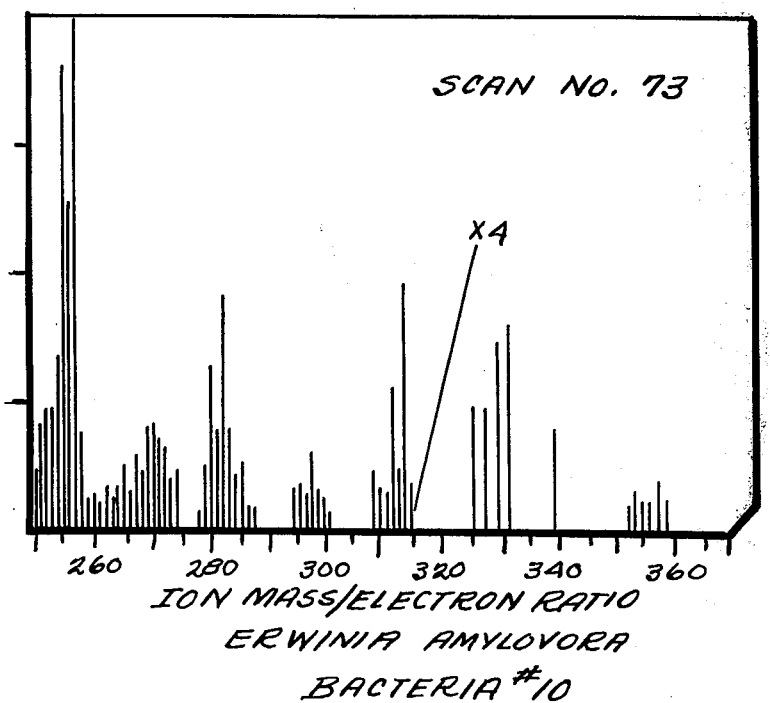

The slotted tip probe shown in FIG. 1B is the invention of another inventive entity. The slotted tip probe comprises two half cylinders 200 and 202 (preferably formed from stainless steel) having mating semi-circular recesses 204 and 206 forming a well for receiving the glass cylinder 208 having a solid sample core therein. The heating element for the slotted tip probe of FIG. 1B comprises the circular disc 210 located at the lower portion of half cylinders 200 and 202. The half cylinders 200 and 202 and connecting electrical leads 212 and 214 provide a supply of electrical heating current which passes through the heating disc 210 (preferably formed from kovar) thus generating heat at the lower end of the sample cylinder 208. A thermocouple 216 is spot welded to the center bottom of the heating disc 210 and the electrical thermocouple leads 218 are communicated back through the probe structure such as through feed-throughs 220. Of course, the electrical leads 212 and 214 also serve to physically position the slotted tip of the probe and are preferably formed of approximately 20 gauge stainless steel. In the preferred exemplary embodiment, the probe tip has a diameter of approximately 0.156 inch, a slot height of approximately 0.175 inch, a slot width of approximately 0.132 inch and a heating disc thickness of approximately 0.0015 inch.

The slotted tip heated solids probe of FIG. 1B is preferred because it appears to provide more accurately reproducible controlled heating of the sample and thereby provide more accurately reproducible measured data results according to the process of this invention.

Using the equipment shown in FIG. 1A, one may analyze, detect and record measured data representing the relative ion intensity at successive or periodic time intervals for a whole spectrum of ion masses and/or for the total ion current. These measured data parameters may be visualized in three dimensions as shown in FIGS. 1C-1F. As shown, for example, in FIG. 1C, the recorded data axes in two dimensions would be relative ion intensity versus ion mass (actually mass to charge ratio, but referred to herein as simply mass, ion mass or mass number, etc.). Furthermore, since such spectral plots of ion intensity versus ion mass may be made at successive or periodic time intervals, there is effectively also a third dimensional data axis, namely, time. In the present process time is uniquely related to sample temperature since the sample is raised in temperature according to a predetermined non-isothermal time dependent function.

Thus, as shown in FIG. 1D, one may obtain a total ion plot of ion current intensity versus time or temperature. Since such a plot takes into account the ion current contributions arising from all ion masses, it is convenient to depict the total ion plot along the zero mass plane as a part of the other time dependent measured data to be recorded for non-zero specific ion masses.

In actual practice, with the exemplary embodiment of apparatus shown in FIG. 1A, the mass spectra (or predetermined masses therein) are sequentially sampled at successive or periodic time intervals as shown in FIG. 1E. Here, the relative ion intensity for specific masses at a given instant of time is represented by a simple bar parallel to the ion intensity axis as will be appreciated in FIG. 1E.

While the mass spectra shown in FIG. 1E at particular instants of time may also be relevant to the classification and/or identification of a biological specimen, the time dependent variations of ion intensity for a particular ion mass are much more significant as shown in FIG. 1F. As will be appreciated, the accumulation of sequential mass spectra data as in FIG. 1E provides the basis for the single ion data plots shown in FIG. 1F as a function of time or temperature. It should now also be noted that the total ion plot of FIG. 1D may be combined with the single ion plots of FIG. 1F to provide a composite of time dependent data for use in comparison and/or cross correlation processes for classifying and/or identifying biological specimen in a manner which is facilitated by this invention.

It should also be noted that an examination of the sequential mass spectra of FIG. 1E may be useful in identifying the specific ion masses necessary and/or more significant for use in the single ion plots of FIG. 1F and for subsequent utilization in the comparison and/or cross correlation classification and identification steps. It will be appreciated that the recorded data represented as three dimensional plots in FIGS. 1C-1F may actually be recorded in the form of three dimensional arrays, or a pair of complementary two dimensional data arrays or other suitable means for recording three dimensional data values as will be appreciated.

As previously noted, this invention involves the recordation of data as a function of time or temperature as shown in FIGS. 1D and/or 1F for one or a library of biological specimen whose classification and/or identity are fully known. Thereafter, the process of this invention is repeated to provide similar recorded data as a function of time or temperature for an unknown biological specimen. The recorded data resulting from the unknown biological specimen is then compared or cross correlated with the sets of recorded data earlier resulting from biological specimen having known classification and or identification. In this manner, the classification and/or identification of the unknown biological specimen is determined by the classification and/or identification of the known biological specimen having previously produced a set of record data which mostly correlates or compares to the data resulting from the unknown specimen. A complete correlation should establish the actual classification and identity to the extent it was available for the "known" specimen in the library of known data. Less than complete match or correlation may still result in at least partial classification within the taxonomic hierarchy for the unknown specimen.

Biological specimen such as organisms are typically grown in a culture medium. Typically, in a purely exemplary embodiment carrying forth this invention, organisms may be harvested (at a consistent point in their growth cycle) from trypticase-soy or 5% sheep's blood agar plates and placed in suspensions of methanol or a suitable killing solvent. Cellular concentration of the suspension will be of the order of $15 \times 10^8$ cell/ml, corresponding to a McFarland nephelometer reading of 5. A sample of approximately $10^7$ cells may be placed into the probe of the mass spectrometer and subjected to the thermal decomposition protocol. Internal standardization of ion intensities will be carried out for each run using a substance with characteristic isotopic distribution greatly different from organism decomposition products. Mass spectral data will be acquired for each decomposition run under the control of a dedicated data handling system. Data gathered in this fashion will then be analyzed for their characteristic features.

The cells used in analysis may be prepared in two ways. First lypholyzed cellular material is introduced directly into the solids probe capillary tube. This form of cellular material has the advantage of handling ease, but has the disadvantage of requiring long preparation time after harvesting of growth. The second form of cell preparation is to harvest cells from an agar slant or plate, and to immediately place them into a suspension. At the time of analysis, the aliquot of the suspension is placed in a sample tube, and the solvent is evaporated from it. This second method of sample handling has the advantage of simplicity and speed.

The amount of cellular material used in a purely exemplary analysis has been 10-100 $\mu$g. Some attempt has been made to analyze nearly equal amounts of material for each organism. This is an important consideration for the comparison of mass spectral intensities from one organism to another, since it is assumed that instrumental sensitivity is relatively constant for a given mass of material. Replication of sample sizes is much easier to accomplish when using the suspension method of sample preparation rather than lypholyzation since suspensions can be prepared to a nephelometry standard.

Bacteria samples are introduced to the chemical ionization mass spectrometer source on the tip of a heatable solids inlet probe. The probe is heated using a linear temperature ramp which runs in this purely exemplary embodiment between ambient and 400° C.

A temperature programmer is used to produce a linear heating ramp with a resolution of 1.6° C in the region of interest. Temperatures at the probe tip are controlled by a feedback loop using the signal from a thermocouple junction at the probe tip. The programmer can be set to operate at three heating rates, 20°, 40° and 80° C per minute, and has been shown to give reproducibly linear temperature response at the probe tip for all three heating rates.

A run is initiated immediately after the bacteria sample is placed into the source by starting the temperature programmers and by beginning data acquisition. The physiochemical processes which occur in the bacterial sample during heating are postulated to be a series of decompositions of the large molecules. The rate of temperature increase is slow compared to established pyrolytic techniques. Therefore the decomposition products are postulated to evolve temporally from the cellular substrate. These decomposition products are swept by the reagent gas into the chemical ionization source. A temperature dependent series of such evolutions at different mass numbers are recorded. The shape of these evolution curves is dependent upon the kinetics of decomposition and to a lesser extent upon the heating rate and sample size.

The fragments of macro-molecules produced at any time in the heating profile yields ions which are characteristic of the bacterial strain being analyzed. These ions often will be at the mass number of the neutral fragmented macro-molecule; they may also represent further fragmentation induced by the ionizing process itself. Coincidence of evolution of particular ionic masses may be characterizers of the bacterial strain but may also provide information about the macro-molecular structure of the bacteria or other biological sample. The data analysis task is to separate and to select characteristic masses by the shape of their evolution patterns.

Chemical ionization of the macro-molecular decomposition products is used in this work because of the minimal, but chemically significant fragmentation which molecules undergo when ionized in this way. Chemical ionization is a process in which ionization of neutral molecules occurs principally, but not exclusively, by the transfer of a proton from a stable ionic species in a plasma (reagent ion) to a neutral species having a higher proton affinity than the reagent ion. The proton transfer process involves the transfer of a small amount of energy to the neutral species, and thereby minimizes the fragmentation in the ionic species. The fragmentation which does occur, because it is less than that occurring in conventional electron impact ionization, provides an optimal amount of information for deducing origins of the various ionic fragments.

The mass spectrometer and data handling system are used in this system as detector and temporary data storage device. The task for the system is to optimize these functions in terms of sensitivity, reproducibility and storage space requirements.

The system detector has been a quadrupole mass spectrometer. The mass spectrometer has been set to scan only a purely exemplary 500 a.m.u. mass range and the entire output of the device recorded. The mass range from 250–750 a.m.u. was selected for monitoring in this exemplary embodiment for several reasons. First, high mass ions are felt to be more characteristic of the macro-molecular composition of the bacteria under study than are low mass ions. Second, chemical ionization produces a large enough number of high mass ions that their detection can be readily accomplished.

Sensitivity considerations in this work to date have been directed towards obtaining uniform performance of the mass spectrometer over the course of many analyses. A calibration mixture of methyl stearate (m/e 299) and chromium tris-1,1,1-trifluoro-2,4-pentanedionate $Cr(tfa)_3$ (m/e 512) is used both to align the mass scale and to maintain a constant ratio of intensities at these two masses. A constant ratio is indicative of consistent performance without a consideration of absolute sensitivity. A second aspect of sensitivity is compensating for the tendency of quadrupole mass filters to decrease their efficiency in ion transmission at high mass numbers. This compensation is achieved principally by increasing data sampling times at the higher mass numbers in comparison to lower mass numbers.

Reproducibility of data generated early in the course of the preliminary work was confirmed by visual inspection of single ion plots. The later work done in the methodology development included use of an objective method for confirming the apparently excellent reproducibility which has been observed in replicate runs. Linear correlation coefficients were calculated using the intensities of each of several specific single ions in replicate runs. Identical spectra would produce correlation coefficients of 1.0, where the value of the correlation coefficient can range between −1.0 and 1.0, zero being indicative of no linear correlation. The detailed technique for performing these calculations is described below.

Storage space requirements are set by the demands of sampling time, mass range and temperature resolution. The objective has been to obtain and store an adequate, but not excessive, quantity of data. The general practice has been to acquire about 150 spectra with an overall repetition rate of about 8 sec, thereby yielding a 3° C temperature resolution. The result of this is to generate 75,000 pieces of information for each analysis.

As stated above, the data produced in one analysis consists of a series of time dependent mass spectra, which are also temperature dependent mass spectra due to the linear relationship of time and temperature. It is an easy task to have the data handling system display the total ion current of each of the approximately 150 spectra in a given run as a function of the sequential scan number. In the preliminary experiments such scans were taken at approximately 8 sec intervals corresponding to about a 3° C temperature change. In a similar fashion the mass spectrum at a given scan number may be displayed, and also the intensity variation of any mass number as a function of scan number (time, temperature) may also be displayed. It is this last type of data format which has been used extensively in data analysis to date.

The temperature dependent evolution of molecular species characteristic of a bacterial organism is shown by analysis of curves such as those in FIG. 1F. This requires the ability to distinguish between organisms as unambiguously as possible as well as the ability to group together organisms which are similar. Analysis of the single ion plots such as FIG. 1F involves determining significant features for characterization. The manner in which the characteristic curves are to be identified has been developed along two approaches which appear to give nearly equivalent results. One of these approaches is strictly empirical, and the other is based on a physiochemical model of the cellular decomposition during the heating protocol. Both methods can be implemented in a computerized search for characteristic features, but the one based on a model process is more attractive in its overall implications. Both methods have been applied to the preliminary data by using manual rather than computer methods.

Once characteristic features have been selected for all bacteria being analyzed, then these features are classified. They were arranged so that the various organisms can be differentiated from each other. When a set of unique features is developed for each of the bacteria, then the classification is trivial. If individual diagnostic features cannot be found, then more elaborate techniques, including pattern recognition, will be applied. The results to date indicate that it may be possible to develop a set of unique features for each of the bacteria of interest, thereby greatly simplifying the task of data analysis.

The empirical method used for feature selection requires that mass spectra from several points in a run be searched visually for ions that are judged to be prominent. A table of candidate ions from all bacteria which may serve as characterizers is produced, and then single ion plots as a function of scan number for each ion in the table is made for each of the bacteria in the study. Visual study of these single ion plots is then undertaken to find those which are judged to have the greatest ability to classify the bacteria. In order to do some testing of the credibility of these visual results, a preliminary mathematical analysis of these results has also been done. The mathematical analysis used single ion plots for each of the bacteria being studied. These were simplified by taking intensities at every tenth scan number between scans 60 and 150. Linear correlation coefficients were then calculated for each organism compared to every other one using the ten point intensity table. The correlation was calculated using the expression:

$$r = \sqrt{\frac{\Sigma x\, y\, -\, \Sigma xy}{[(n\Sigma x^2 - (\Sigma x)^2)(n\Sigma y^2 - (\Sigma y)^2)]}}$$

The results from the calculating of these correlation coefficients tend to confirm the visual analysis of the subjectively selected ions.

The model dependent analysis of the data used the value of the integral of a single ion intensity at various points in the temperature dependent evolution curve (FIG. 1F). By selecting the proper range over which the integrals are to be taken, the occurrence of evolution peaks characteristic of individual decomposition reactions can be readily detected. It is these individual decompositions, occurring at particular mass numbers, which will be taken as the characteristic features to be selected. To date, this data reduction has been done by hand, and therefore the integration range was taken as 50 scans. Nevertheless, even this very crude resolution permitted the differentiation of most of the organisms studied to date.

The process has been performed demonstrating its feasibility for characterizing a test set of 24 bacterial organisms. Both known and unknown samples were analyzed. These initial characterizations were based on perceived visual differences in single ion plots. These differences were confirmed by calculations of linear correlation coefficients.

Table I below lists the 24 organisms analyzed to date.

The list is divided into two parts. The ten bacterial strains at the top were obtained from American Type Culture Collection, Rockville, Maryland. These were prepared by using 10% innoculation of 250 ml of nutrient broth, culturing for 24 hours, and harvesting the organisms. They were then spun down, washed in 0.1 M phosphate buffer and lypholyzed

TABLE I

|  | Total # Runs | Blind Sample |
| --- | --- | --- |
| Bacillus subtilis ATCC #6051 | 10 |  |
| Bacillus megaterium ATCC #14581 | 20 |  |
| Pseudomonas putida ATCC #12633 | 10 |  |
| Pseudomonas putida ATCC #15073 | 10 |  |
| Pseudomonas fluorescens ATCC #13525 | 10 |  |
| Arthrobacter oxydans ATCC #14358 | 10 |  |
| Arthrobacter globiformis ATCC #8010 | 10 |  |
| Escherichia coli ATCC #4147 | 10 |  |
| Escherichia coli ATCC #11775 | 10 |  |
| Erwinia amylovora ATCC #15580 | 10 |  |
| Pseudomonas putida (hospital strain) | 2 | 2 |
| Pseudomonas aeruginosa (L. Madrigal #3400) | 2 | 5 |
| Pseudomonas aeruginosa (W. Bernett #3047-1) | 2 | 6 |
| Pseudomonas aeruginosa (F. Newborn #5901) | 2 | 7 |
| Pseudomonas maltophilia | 2 | 8 |
| Flavobacterium | 2 | 10 |
| Proteus mirabilis | 2 | 11 |
| Providencia stuartii | 2 | 13 |
| Citrobacter freundii | 10 | 14 |
| Citrobacter diversus | 2 | 15 |
| Citrobacter freundii | 8 | 16 |
| Serratia marscens (S. Philipis #1027) | 2 | 17 |
| Serratia marscens (M. Williams #3475) | 2 | 18 |
| Serratia marscens (S. McGee #2445) | 2 | 19 | for 18 hours in two vials. Bacteria received were stored in a refrigerator at 4° C. Samples for analysis were prepared by opening a sample vial, extracting a portion of dried cells using a flamed spatula, putting the cells onto a flammed watchglass, re-plugging the sample tube and placing it into a flamed test tube sealed with a sterile gauge swatch, then replacing the test tube in the refrigerator. Only one vial was open in the laboratory at a time, and all items in contact with the organisms were flamed between openings. Approximately 100 μg of dried cells (approximately 3 × 10$^7$ cells) were placed in a flamed open ended capillary tube, which was then put into a heatable solids inlet probe of the BIOSPECT chemical ionization mass spectrometer.

The second group of 14 organisms were obtained from Dr. Frank Kocka, Billings Hospital, University of Chicago. These were sent on trypticase-soy agar slants, and were maintained by storage at 4° C and by occasional transfer to new slants. The samples were streaked out onto prepared trypticasesoy-5% sheepblood agar plates (BIOQUEST lot # K4ZMMA). The growth on each plate was harvested after approximately 18 hours incubation at 37° C. The harvested organisms were placed in approximately 1 ml methanol in conical bottom tubes. The tubes containing the harvested growth were stored in a refrigerator at 4° C. Samples were prepared for introduction to the mass spectrometer by taking a 6 μl aliquot of the suspension into an open capillary. The solvent was pumped off at ambient temperature and placed in the probe tip. The concentration of organisms in the suspensions can be estimated using McFarland nephelometer standards. The suspensions used were all much more concentrated than 30 × 10$^8$ cells/cc, thus a lower limit for each analysis is 1.8 × 10$^7$ cells. The identity of these fourteen samples was kept secret during data acquisition.

A standard BIOSPECT chemical ionization mass spectrometer was tuned so that approximate unit mass resolution at m/e 512 ($Cr(tfa)_3H+$) was obtained. Other instrumental conditions were a source pressure of 1 torr methane, 0.1 mA emission current, and medium pre-amp gain at half scale multiplier high voltage. Source temperature was maintained throughout at 160° C.

The cellular sample was introduced into the mass spectrometer through the solids inlet. The linear probe heater supply was connected to the probe prior to the sample being introduced, and set to scan at 20° C/min. A run was initiated by sealing the source block with the probe tip and starting the computer scan and temperature program. Scan conditions used in these experiments were:

mass range: 250–750 a.m.u.
data taking time/a.m.y.:
   3 msec (250–350)
   10 msec (351–450)
   20 msec (451–750)
time between sequential scans: 1 sec.

These run conditions were chosen as a compromise between maximizing the signal to noise ratio and losing information due to excessive scan times. A total time of 8.3 sec. between sequential scans with more time spent observing high mass ions seems such a compromise. Data taking was terminated when the high temperature peak had substantially diminished, about 150 scans, with the temperature at 400° C.

The total number of runs on each organism is given in Table I. The large number of runs for the first ten organisms reflects replicate runs during the development of methodology. These results represent a number of approaches to generating data, and it is only the last two or three of each set which are valid replicates of the currently accepted method. On the other hand, there are sufficient similarities between the early and later runs to be confident of overall decomposition techniques.

Of the 14 samples analyzed blind, No. 14 and 16 were shown to be nearly identical, an observation confirmed by Table I. Further checking about the origin of these two samples showed that they were parallel cultures of the same isolate, and for that reason, some small differences might be expected in their decomposition patterns. At the present level of analysis, no such differences were found. The other twelve members of this data set were judged to be distinguishable from each other based on an analysis of single ion plots of the type shown in FIG. 1F.

Reproducibility of the data in these preliminary experiments was shown by the method of linear correlation coefficients. Taking 10 point intensity vectors of single ion plots from several replicate runs of a particular organism, an average vector for the replicates was calculated by summing intensities at each scan number and dividing by the number of replicates. Correlation coefficients were then calculated for each run compared to both the average and to the other runs. This was done for two organisms at several mass numbers. Table II shows the results for the calculation at two different mass numbers, m/e 259 and 261:

TABLE II

| Run Name | Correlation Coefficients for Replicate Runs | | | | | | |
|---|---|---|---|---|---|---|---|
| | 14-1 | 14-2 | 14-3 | 14 avg | 16-1 | 16-2 | 16-avg |
| m/e 259 | | | | | | | |
| 14-1 | 1.000 | | | | | | |
| 14-2 | .969 | 1.000 | | | | | |
| 14-3 | .971 | .978 | 1.000 | | | | |
| 14-avg. | .993 | .976 | .980 | 1.000 | | | |
| 16-1 | .984 | .985 | .987 | .980 | 1.000 | | |
| 16-2 | .939 | .949 | .972 | .929 | .976 | 1.000 | |
| 16-avg. | .966 | .973 | .986 | .959 | .994 | .994 | 1.000 |
| m/e 261 | | | | | | | |
| 14-1 | 1.000 | | | | | | |
| 14-2 | .930 | 1.000 | | | | | |
| 14-3 | .965 | .960 | 1.000 | | | | |
| 14-avg. | .949 | .990 | .974 | 1.000 | | | |
| 16-1 | .946 | .961 | .994 | .965 | 1.000 | | |
| 16-2 | .979 | .906 | .976 | .926 | .961 | 1.000 | |
| 16-avg. | .971 | .944 | .996 | .956 | .991 | .989 | 1.000 |

The results are given in a form which is symmetrical about the diagonal, each table being laid out similarly. Columns one through four are results for organism 14, with column four being the average of the three runs; columns five through seven are results for organism 16 with column seven being their average. The rows are named in the same order as the columns. The number located at the intersection of any row and column represents the value of the linear correlation coefficient, $r$, for those two runs, e.g., the value of $r$ for 14-3 and 14-1 is 0.971; the linear correlation of each of the four replicates of organism 14 with their average values is given in the row labeled 14-average. The linear correlation coefficients of the three replicates of organism 14 with their averages is very high at m/e 259 and is lower than 0.95 for only one run at m/e 261. The linear correlation coefficients of the two replicates of organism 16 with their average is very high at both m/e 259 and 261. The degree of linear correlation between the two average values for the two organisms tends to confirm the inability to separate them by visual means.

The method for selecting characteristic features, and the success of this method can be illustrated using results from the first ten bacterial strains. Throughout the remainder of this discussion, the bacteria are labeled by numbers which correspond to the order in which they are listed on Table III:

TABLE III

| Bacteria Numbering Scheme | |
|---|---|
| Bacteria Number | Identity of Bacteria |
| #1 | *Pseudomonas putida* ATCC #12633 |
| #2 | *Pseudomonas putida* ATCC #15073 |
| #3 | *Pseudomonas fluorescens* ATCC #13525 |
| #4 | *Escherichia coli* ATCC #4147 |
| #5 | *Escherichia coli* ATCC #11775 |
| #6 | *Bacillus magaterium* ATCC #14581 |
| #7 | *Bacillus subtilis* ATCC #6051 |
| #8 | *Arthrobacter oxydans* ATCC #14358 |
| #9 | *Arthrobacter globiformis* ATCC #8010 |
| #10 | *Erwinia amylovora* ATCC #15580 |

Some of the data recorded according to this invention for this preliminary universe of ten different bacteria is present in FIGS. 2–31. For example, the even numbered FIGS. 2–20 portray the total ion current as a function of time or temperature for each of the ten different bacteria while the odd numbered FIGS. 3–21 represent one of the sequential mass spectra taken for each of the ten different bacteria at some specific portion of the thermal degradation process. Ten different single ion plots versus time or temperature are presented for ten specific ion masses in FIGS. 22–31 for each of the ten different bacteria. The specific ion mass presented in each of the different figures is set forth in the following table:

| Ion Mass Utilized in Single Ion Plots | Figure Number |
|---|---|
| 259 | 22 |
| 261 | 23 |
| 276 | 24 |
| 299 | 25 |
| 308 | 26 |
| 311 | 27 |
| 313 | 28 |
| 314 | 29 |
| 391 | 30 |
| 523 | 31 |

Mass spectra from several points in a run for each of the 10 bacteria were visually searched for prominent ions. A table of candidate ions to serve as characterizers is produced, and then single ion plots as a function of scan number for each ion in the table is made for each of the bacteria in the study. The most recent study of these 10 bacteria resulted in a 77 ion table. Single ion plots for all 77 ions for each of the 10 bacteria were then produced. Study of these single ion plots was then undertaken to find those which are judged to have the greatest ability to classify the bacteria. The results of this most recent study are shown in the flow charts of FIGS. 32–33 and single ion plots of FIGS. 22–31.

Figure 32:
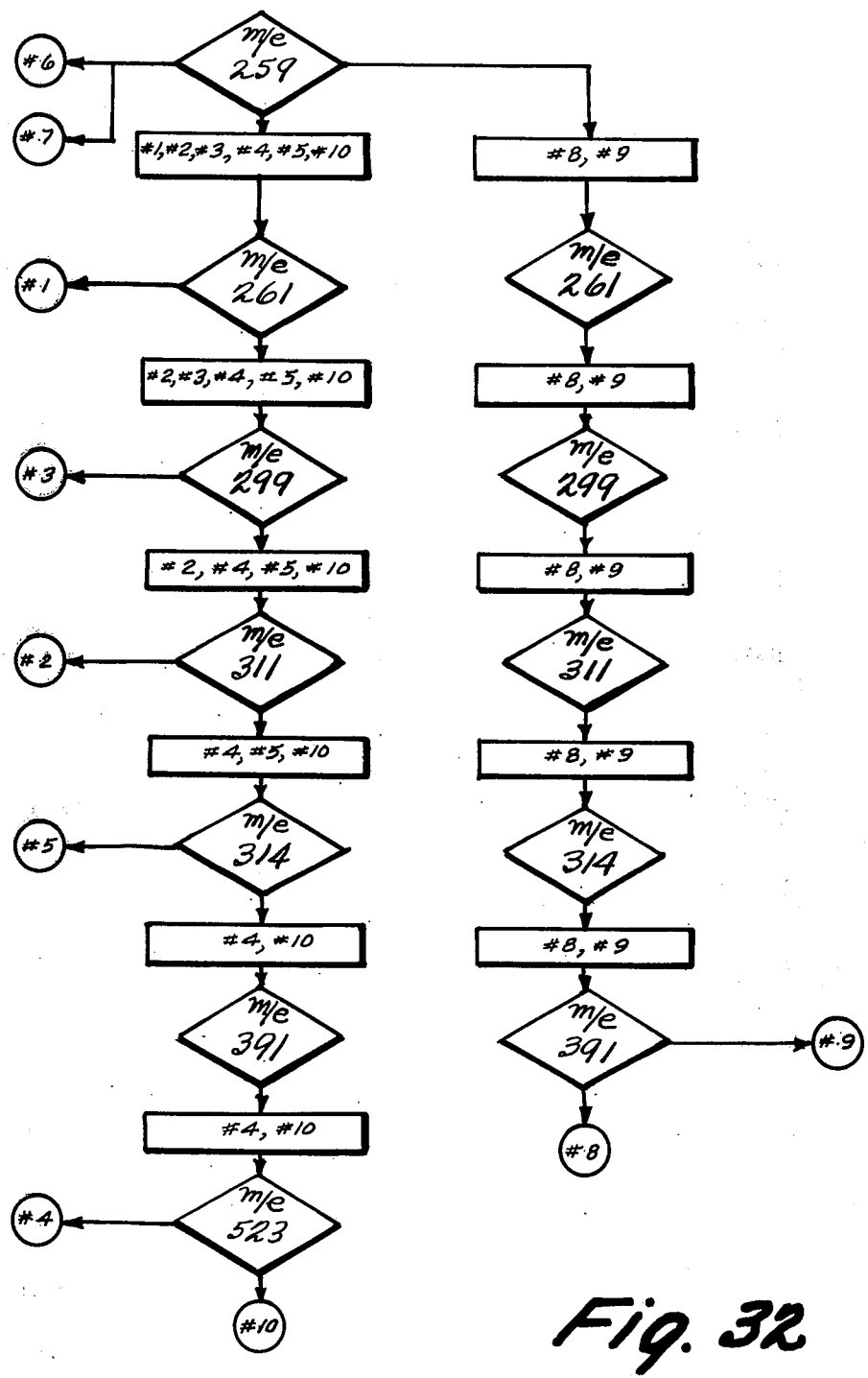
FIG. 32 is a schematic block diagram depiction of an exemplary unknown organism differentiation sequence that may be utilized for processing the recorded data resulting from this invention and classifying and/or identifying an unknown bacteria with respect to the ten types of bacteria referenced in FIGS. 2 – 31.
Figure 33:
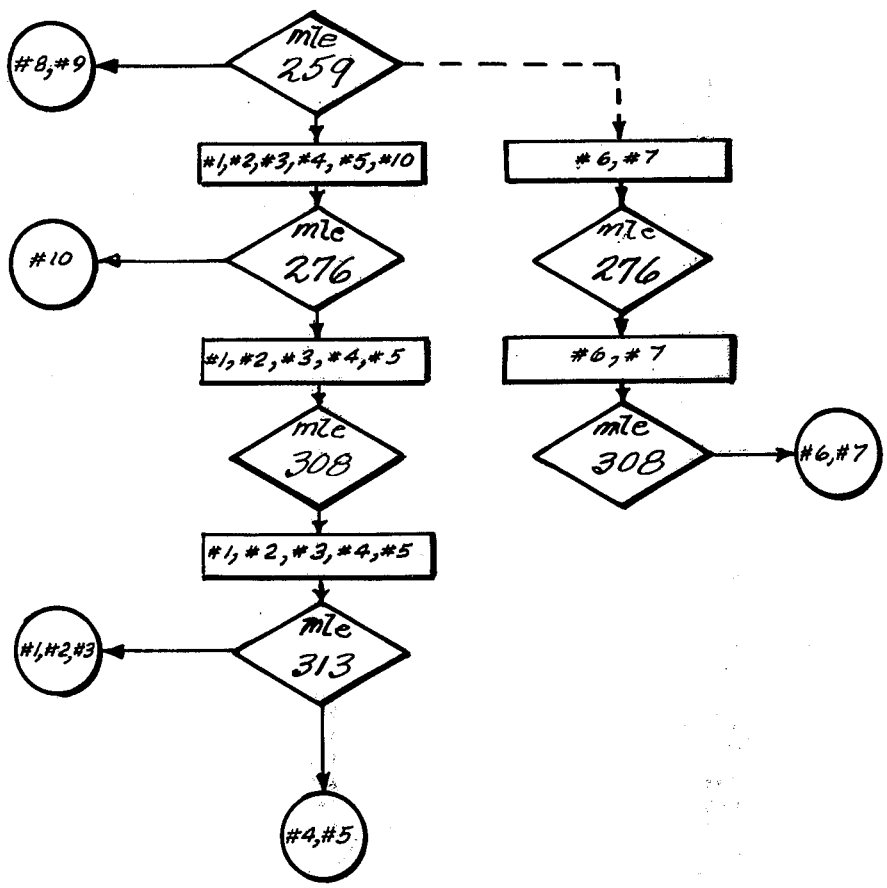
FIG. 33 is a schematic depiction of an exemplary unknown organism genera differentiation sequence also related to the ten different types of bacteria giving rise to the data set forth in FIGS. 2 – 31.
Figure 34:
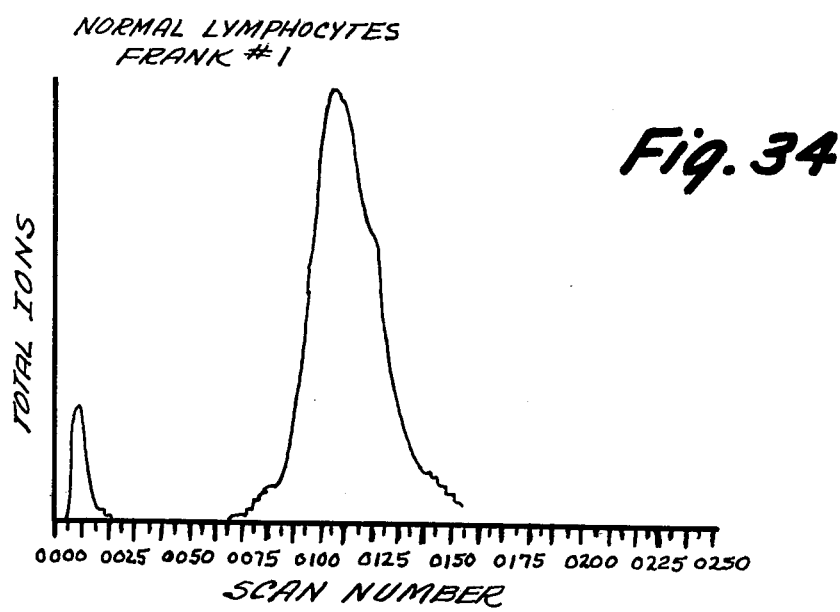
Figure 35:
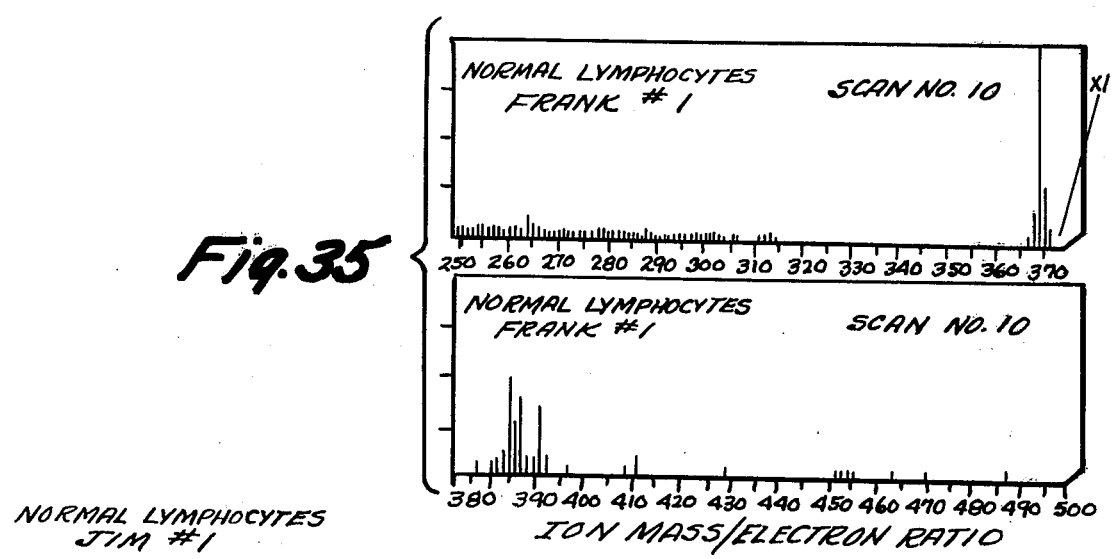
Figure 36:
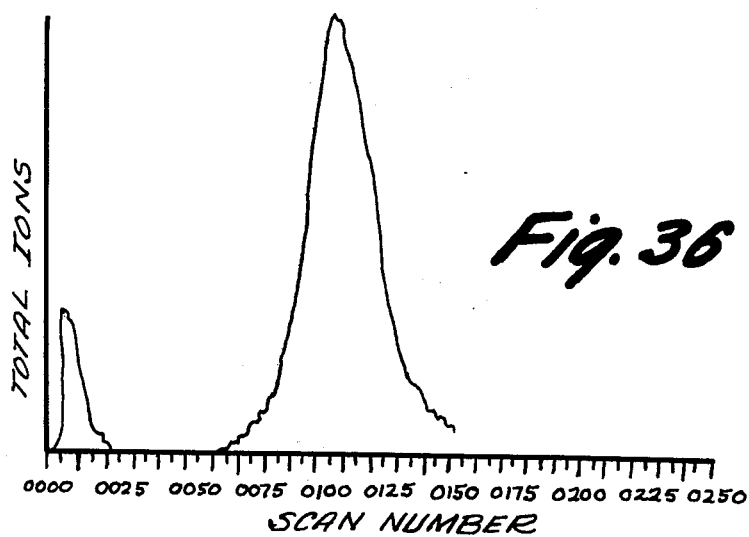
Figure 37:
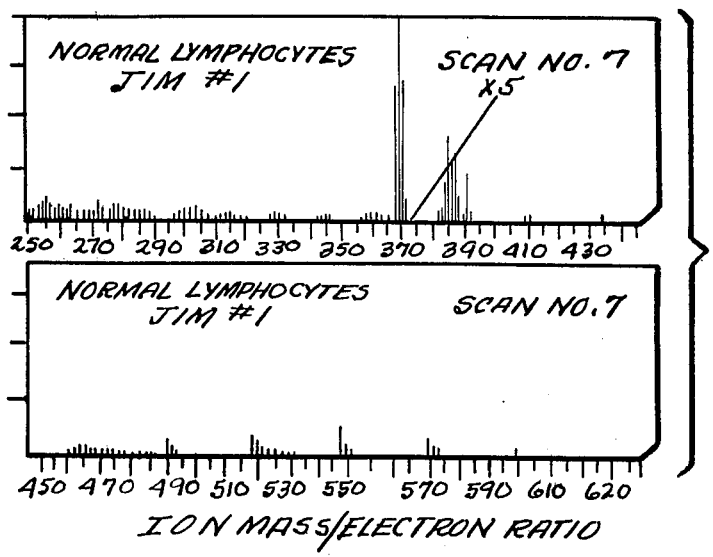
Figure 38:
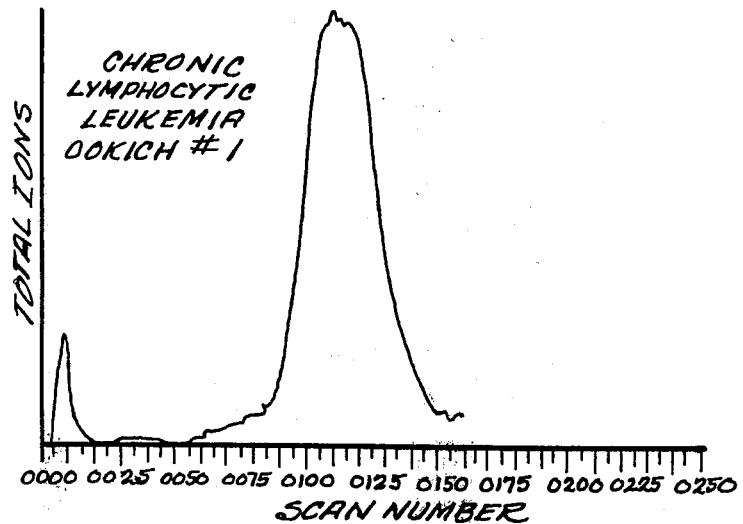
Figure 39:
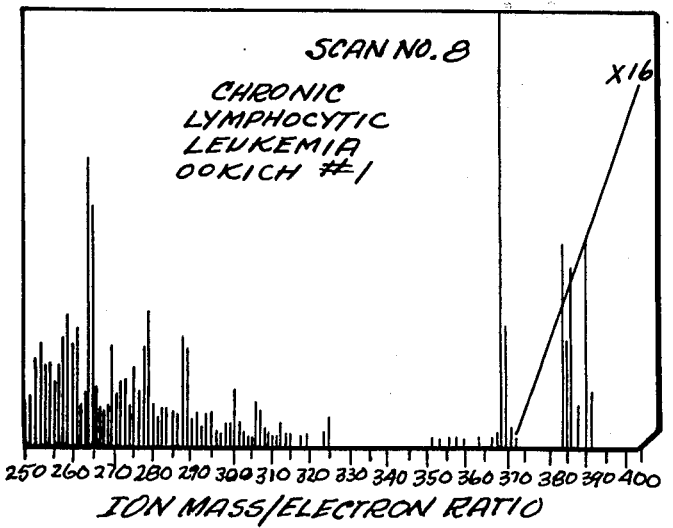

In FIGS. 32–33, the diamonds represent points where separations occur, the organisms separated out appear in circles and the organisms in boxes are organisms unseparated.

FIG. 32 is an exemplary flow chart for differentiations. For the single ion plots at m/e 259, FIG. 22, it is clear that organisms 6 and 7 are different from all the others present and from each other, organisms 8 and 9 are different from the remaining 6, but similar to each other, and that organisms 1, 2, 3, 4, 5 and 10 resemble each other. For the single ion plot of m/e 261, FIG. 23, it is clear that organism 1 is differentiated from 2, 3, 4, 5 and 10, but no separation of 8 and 9 occurs. Those separated previously are no longer considered, but are carried on the chart for uniformity. For the single ion plot of m/e 299, FIG. 25, organism 3 is separated, and so forth for the other plots, FIGS. 27, 29, 30 and 31.

It is also possible to classify the data into genera. FIG. 33 shows the flow chart for this grouping. For the single ion plot of m/e 259, three groupings result: organisms 8 and 9 are similar to each other and different from all others and are the two representatives of genus Arthrobacter (this pairing is seen in most of the other single ion plots), organisms 6 and 7 are different from each other, but different in a rather specific way from the other six as well. Finally, organisms 1, 2, 3, 4, 5 and 10 are all fairly similar. The plot for m/e 276 separates organism 10 from 1, 2, 3, 4 and 5 (looking especially at the higher scan numbers) and is the representative of genus Erwinia. M/e 308 shows the grouping for organisms 6 and 7, the genus Bacillus organisms. M/e 313 shows that organisms 4 and 5, genus Escherichia, are grouped thereby leaving the three organisms in genus Pseudomonas grouped by default. To summarize, Pseudomonas has a particular shape at m/e 257 that is shared by Escherichia and Erwinia, but is different at m/e 276, which groups Erwinia, and at m/e 313, which groups Escherichia.

Both the differentiation and grouping of FIGS. 32 and 33 are intended to show the operational principles of the pattern recognition techniques and are not meant to be limitive in the use of any particular mass number.

Correlation coefficients have been calculated in a fashion similar to that used in the reproducibility study, but they are now used as a means of distinguishing between organisms. Caution should be used in relying too heavily on these values since they are based on single replicates; nevertheless, they appear to illustrate the point. These correlation coefficients results are shown in Table IV and represent the correlation of each organism compared to itself and every other one.

Figure 22:
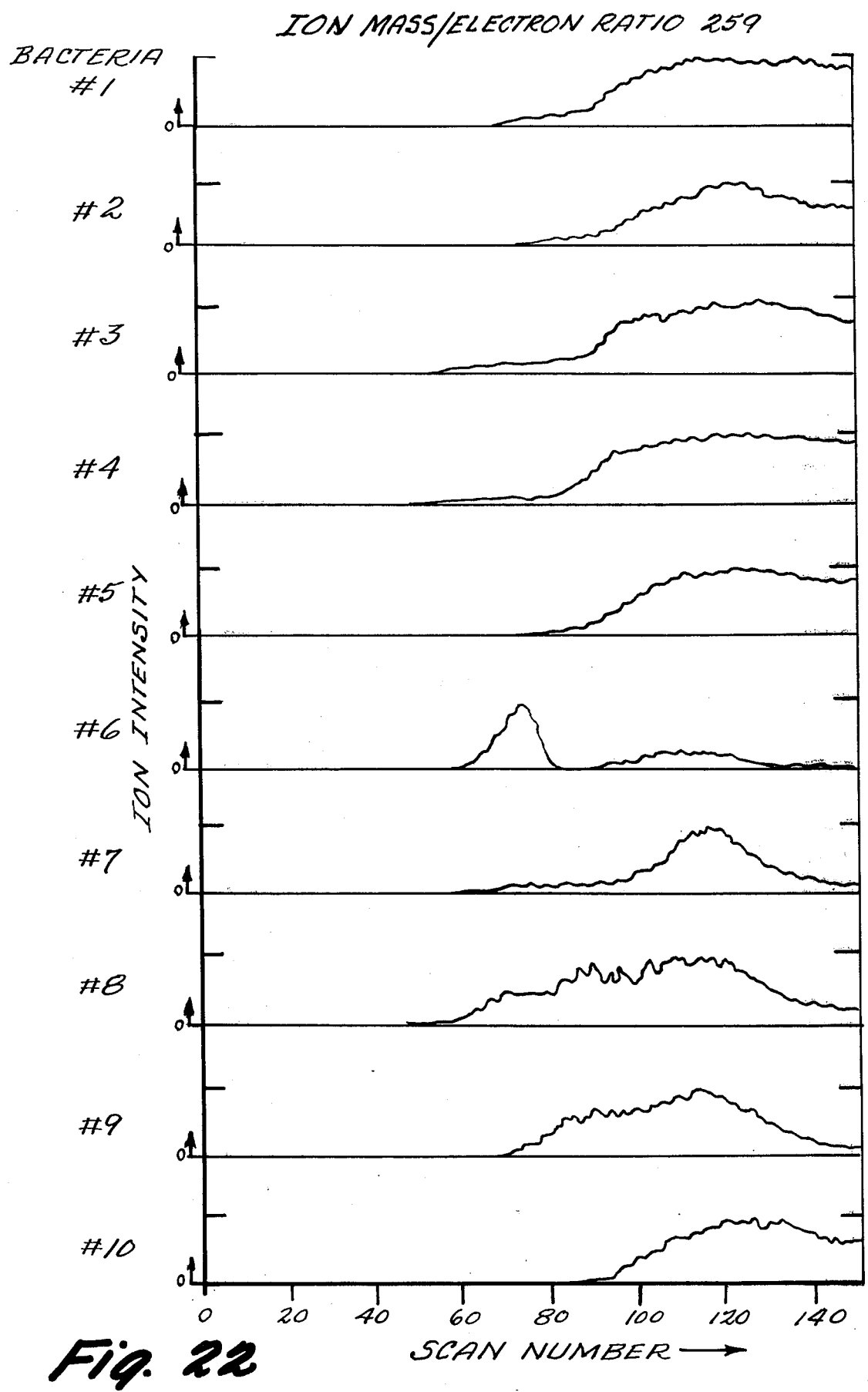
FIGS. 22 – 31 are plots of relative ion intensity versus time or temperature of various specific ion masses for each of the ten different types of bacteria utilized and referenced in FIGS. 2 – 21.
Figure 23:
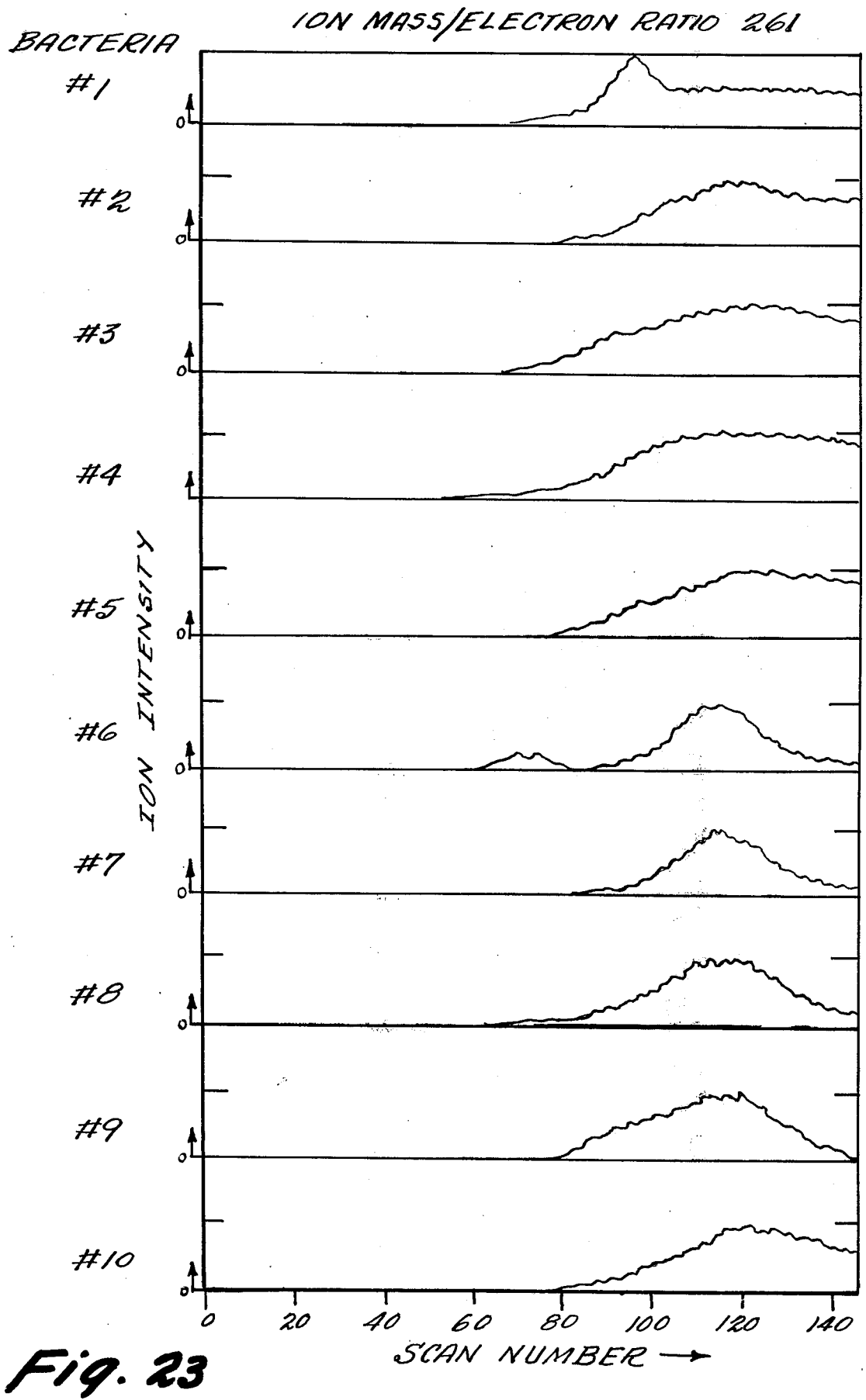
Figure 24:
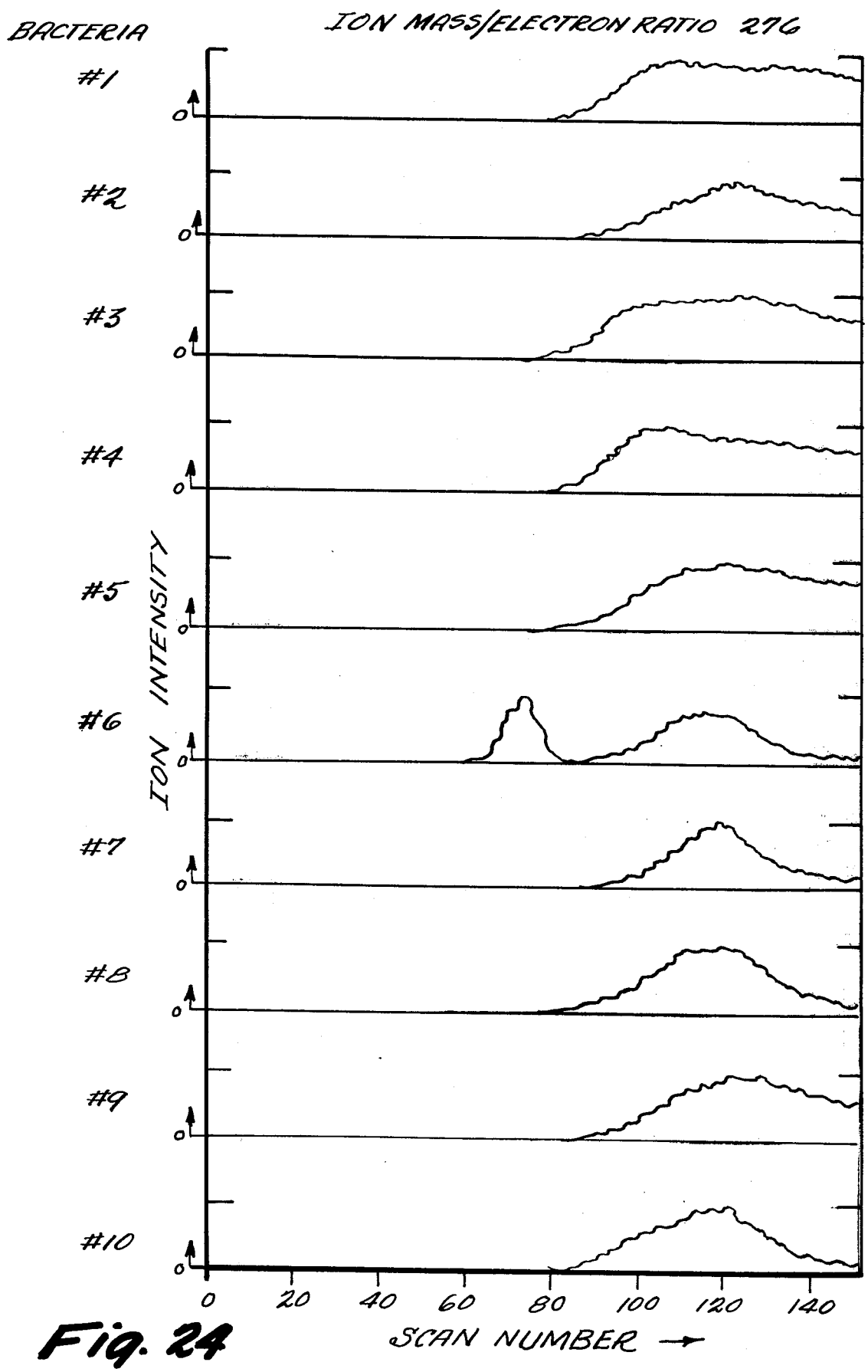
Figure 25:
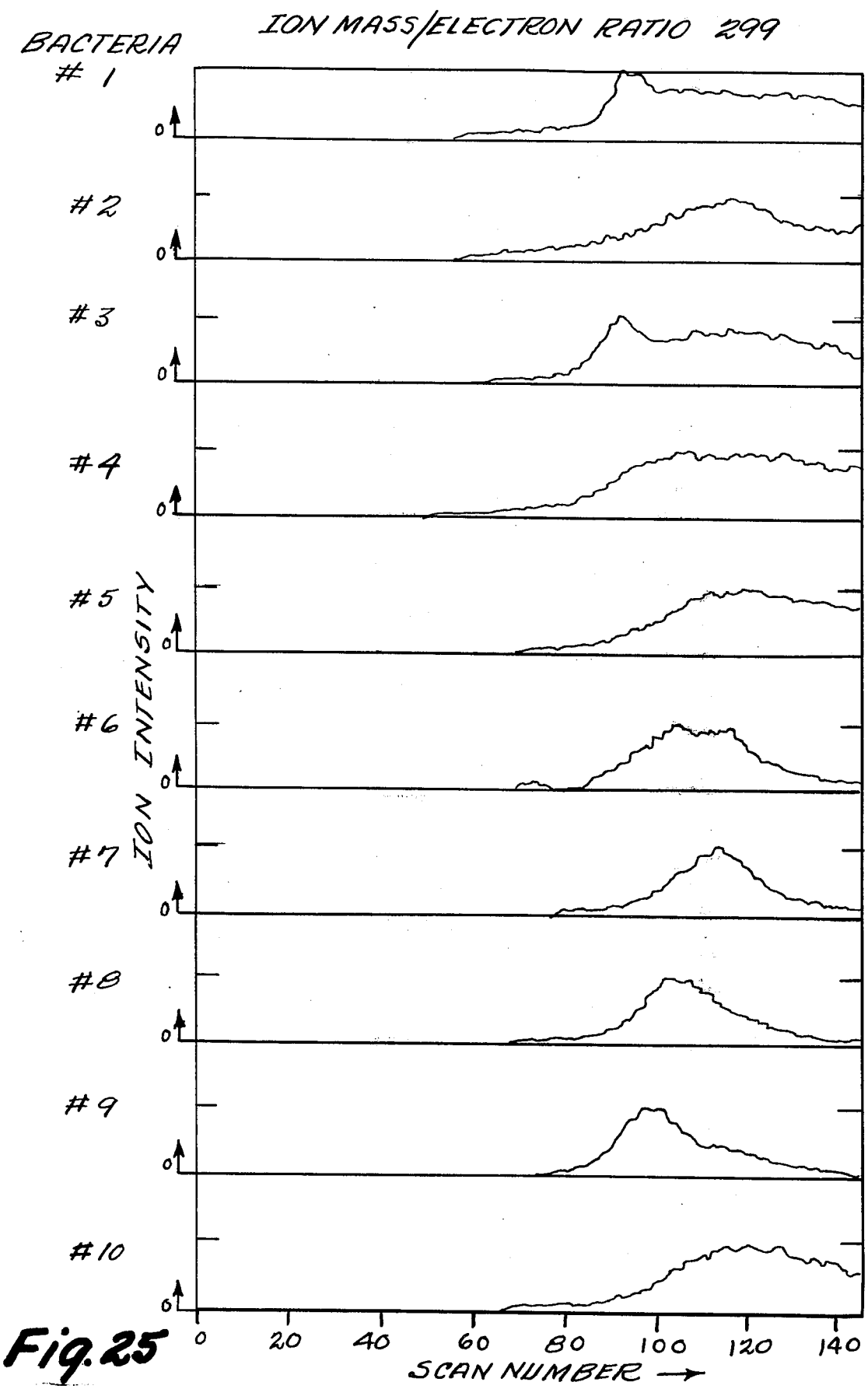
Figure 26:
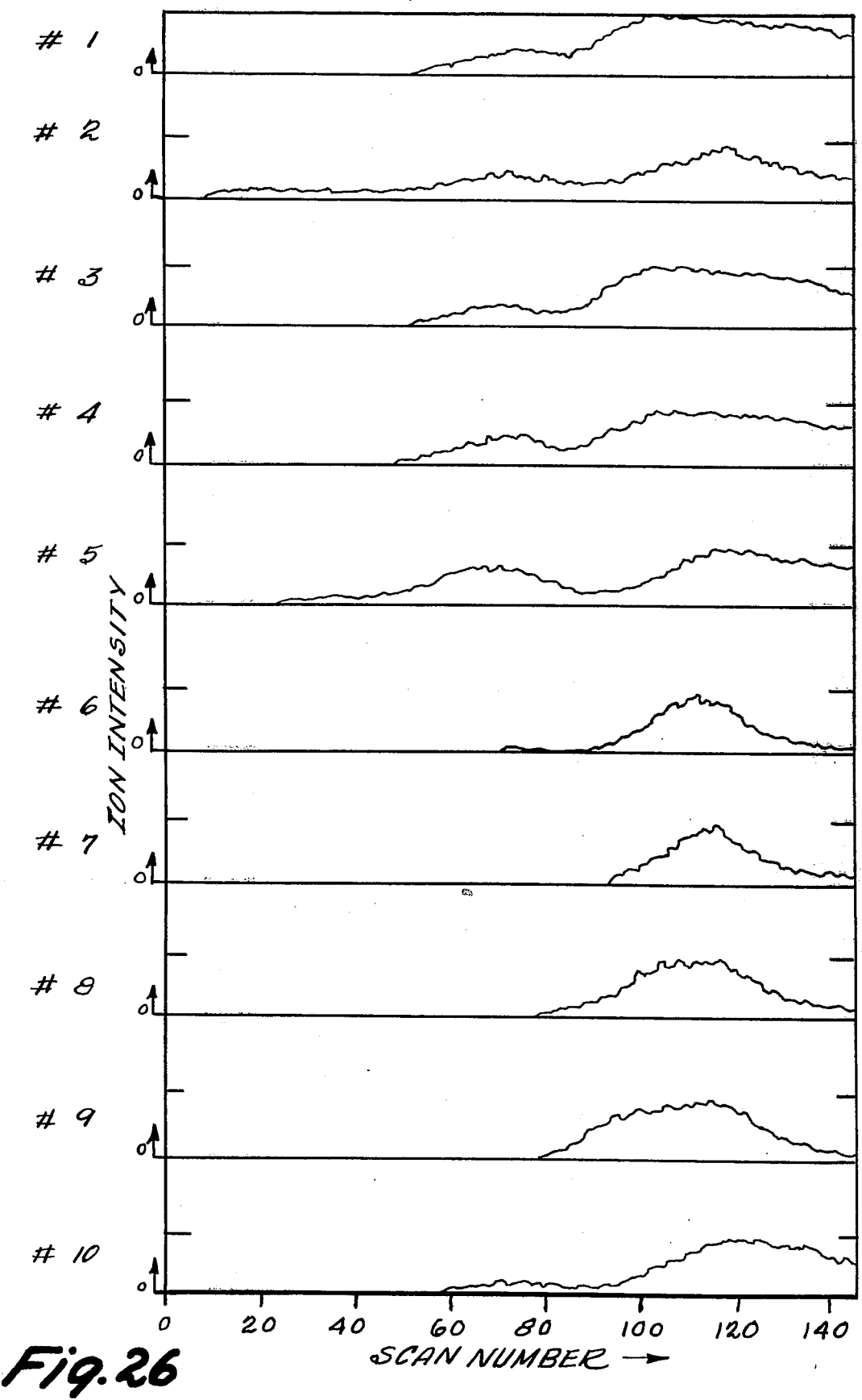
Figure 27:
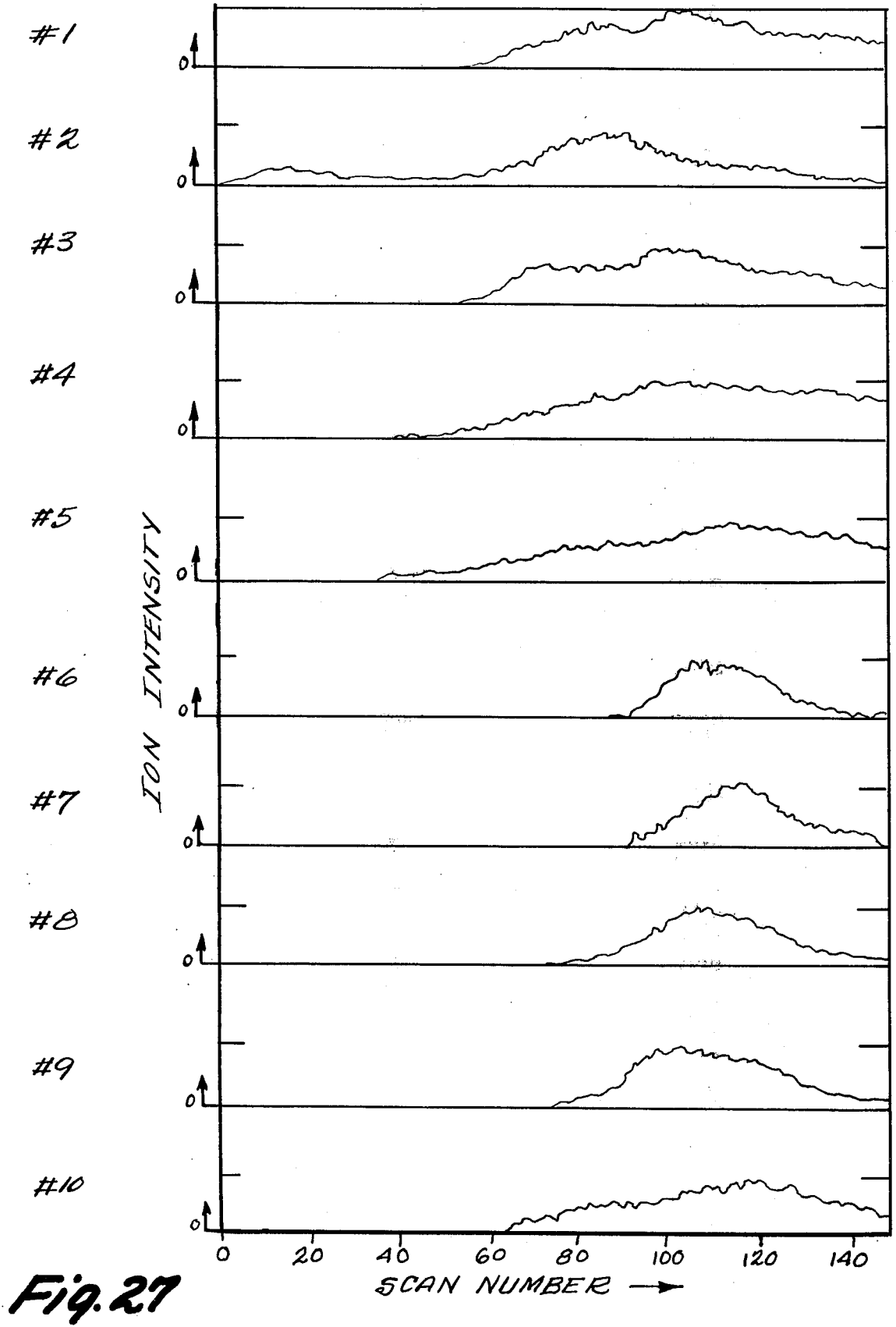
Figure 28:
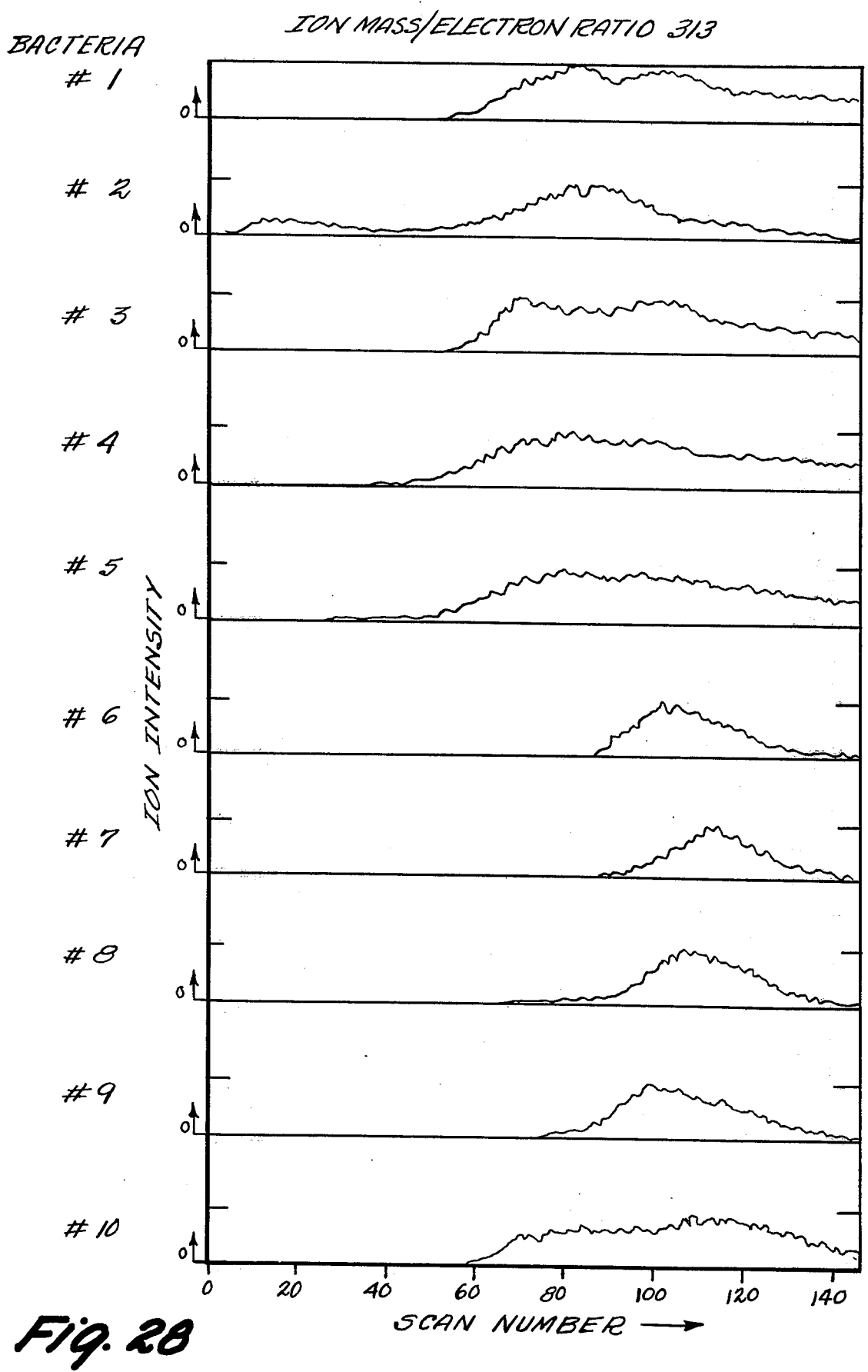
Figure 29:
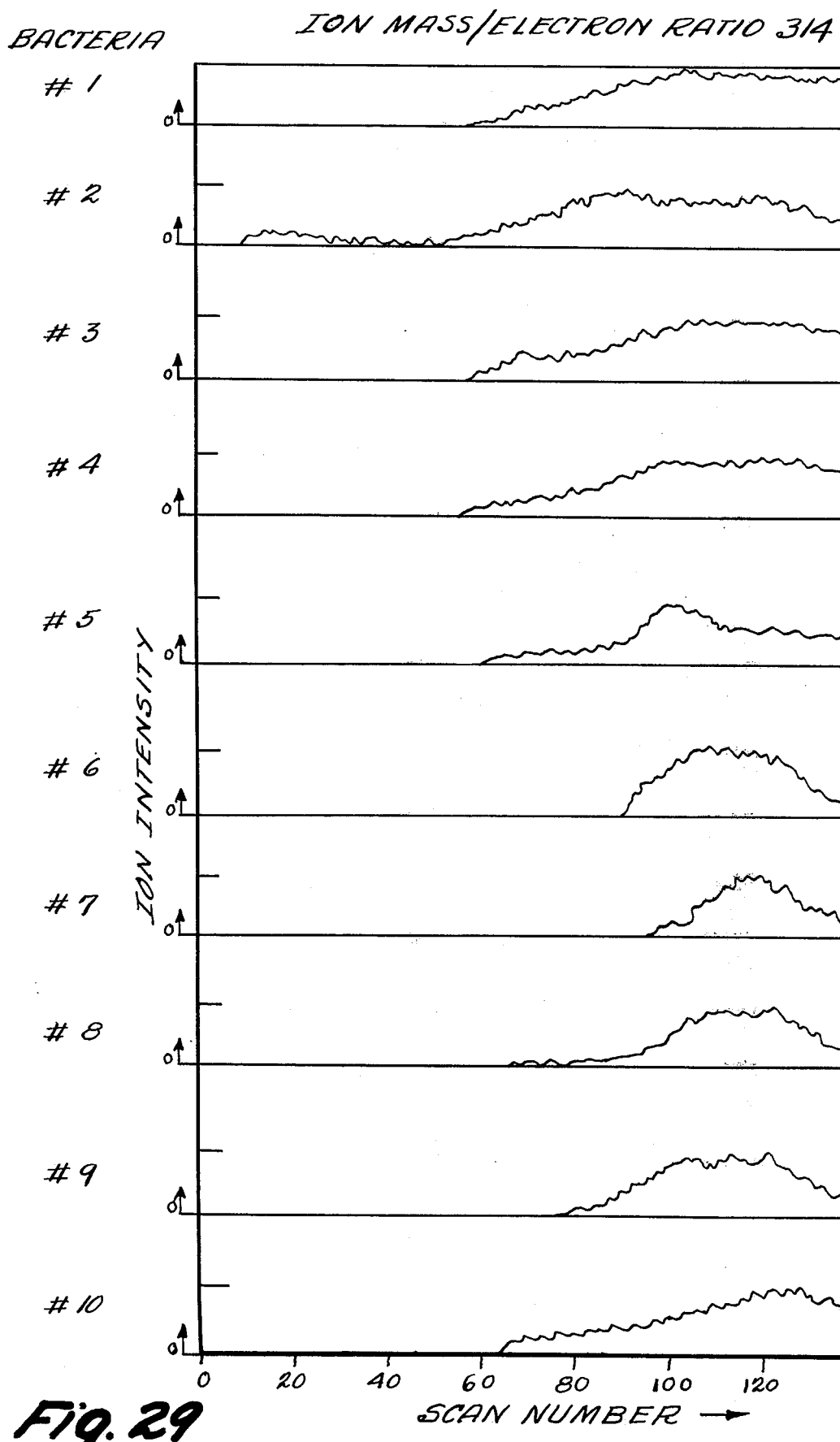
Figure 30:
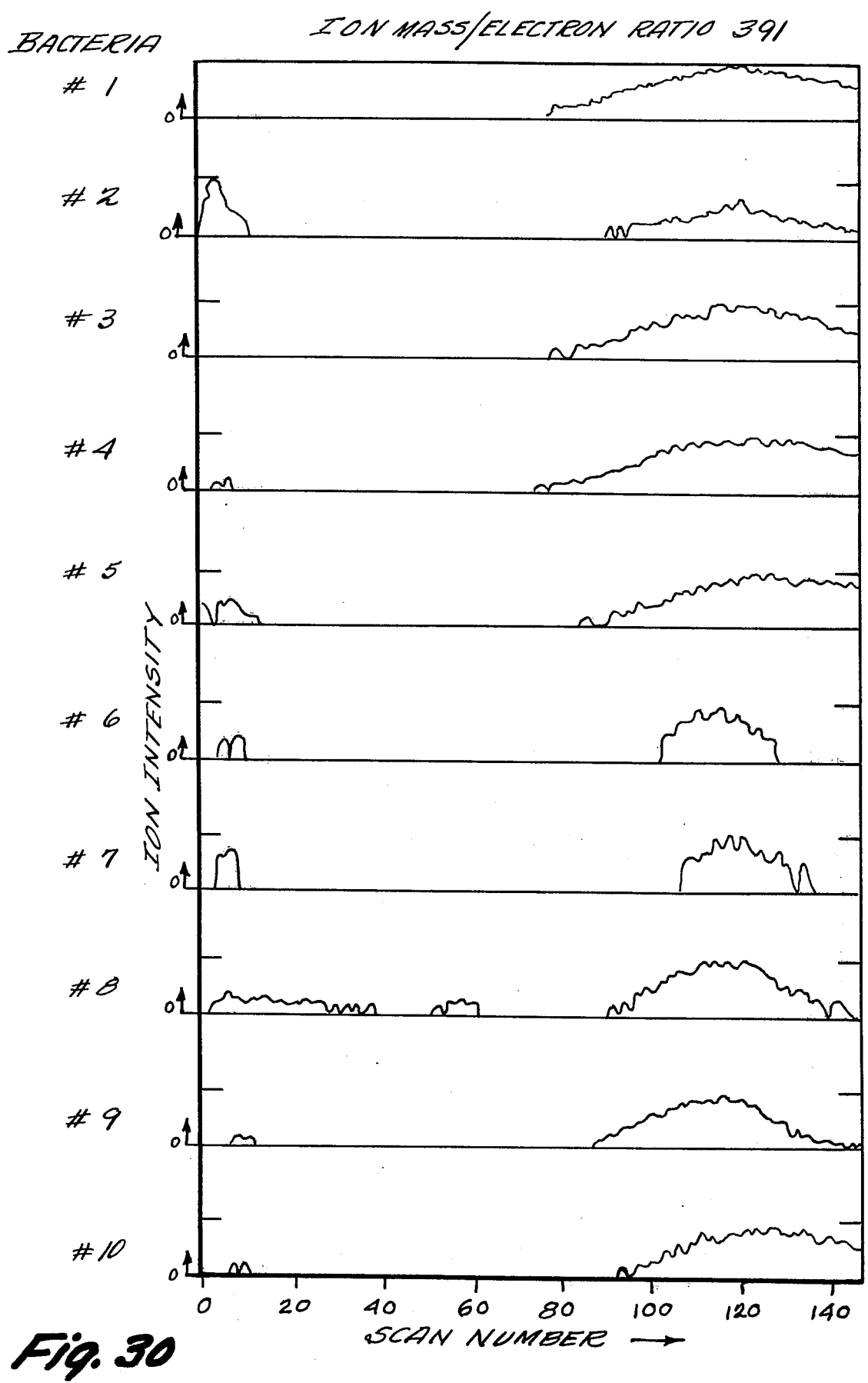
Figure 31:
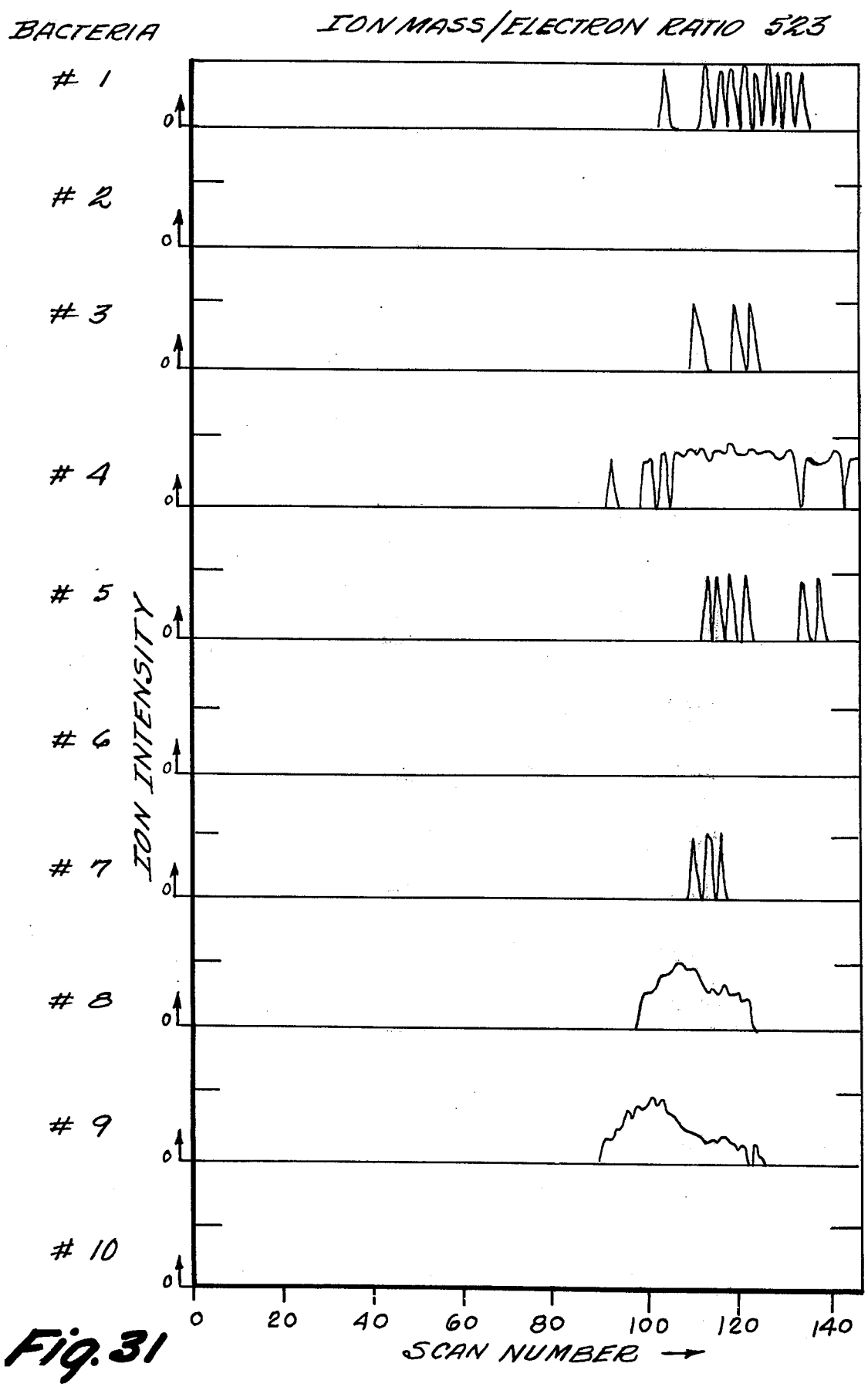

The calculation shown in Table IV was performed at two mass numbers, m/e 259 and m/e 261. The similarity at m/e 259 between organisms 1, 2, 3, 4, 5 and 10 seen in FIG. 22 is confirmed by the appropriate entries in the first column of Table IV. In addition, the marked differences between organisms 6 and 7 and the other eight seen at m/e 259 is confirmed by the eleven off-diagonal entries for these two. Finally, the resemblance noted between organisms 8 and 9 is confirmed by the entry in row nine of column eight, i.e., 0.950. The separation of organism 1 from organisms 2, 3, 4, 5 and 10 at m/e 261 which was shown in FIG. 23 is confirmed by the entries in the first column of the m/e 261 portion of Table IV. Furthermore, the continued resemblance of organisms 2, 3, 4, 5 and 10 is shown by the entries in those columns. The similarity of organisms 8 and 9 is also shown in this portion of Table IV.

TABLE IV

Linear Correlation Coefficients Between Ten Organisms

| Organism Number | 1 | 2 | 3 | 4 | 5 | 6 | 7 | 8 | 9 | 10 |
|---|---|---|---|---|---|---|---|---|---|---|
| m/e 259 | | | | | | | | | | |
| 1 | 1.000 | | | | | | | | | |
| 2 | .973 | 1.000 | | | | | | | | |
| 3 | .984 | .983 | 1.000 | | | | | | | |
| 4 | .952 | .989 | .981 | 1.000 | | | | | | |
| 5 | .983 | .992 | .972 | .971 | 1.000 | | | | | |
| 6 | −.381 | −.429 | −.382 | −.419 | −.443 | 1.000 | | | | |
| 7 | .780 | .713 | .772 | .716 | .725 | .022 | 1.000 | | | |
| 8 | .360 | .328 | .425 | .400 | .275 | .432 | .688 | 1.000 | | |
| 9 | .560 | .550 | .639 | .623 | .497 | .196 | .802 | .950 | 1.000 | |
| 10 | .985 | .960 | .958 | .939 | .979 | .369 | .705 | .319 | .522 | 1.000 |
| m/e 261 | | | | | | | | | | |
| 1 | 1.000 | | | | | | | | | |
| 2 | .711 | 1.000 | | | | | | | | |
| 3 | .778 | .971 | 1.000 | | | | | | | |
| 4 | .776 | .975 | .990 | 1.000 | | | | | | |
| 5 | .721 | .981 | .973 | .984 | 1.000 | | | | | |
| 6 | .406 | .722 | .664 | .625 | .587 | 1.000 | | | | |
| 7 | .512 | .865 | .824 | .783 | .765 | .945 | 1.000 | | | |
| 8 | .637 | .841 | .854 | .799 | .762 | .899 | .958 | 1.000 | | |
| 9 | .713 | .824 | .859 | .807 | .745 | .882 | .928 | .981 | 1.000 | |

TABLE IV-continued

| | | Linear Correlation Coefficients Between Ten Organisms | | | | | | | | |
|---|---|---|---|---|---|---|---|---|---|---|
| 10 | .602 | .957 | .943 | .940 | .976 | .603 | .784 | .779 | .726 | 1.000 |

The analysis based on the physical model of the decomposition demonstrates the same point.

Calibration of the probe tip temperature is preferably carried out using a well characterized thermal decomposition. The de-polymerization of polymethylmethacrylate has been shown to occur between 318° and 381° C, maximum at 365° C, for a heating rate of 1° C/min. Use of a higher heating rate, such as the 20° C/min. in the proposed work, will serve to both lower the maximum and narrow the peak. Both of these effects are predictable in their extent, and the point of occurrence at several heating rates will be measured to confirm these predictions.

Absolute intensity calibrations are also preferably carried out. The usual method used to align the mass scale and to monitor relative instrumental sensitivity should preferably be expanded to include absolute intensity calibration of every decomposition run. This may be done, for example, by monitoring signal intensity of $[Cr(tfa)_3H]^+$ m/e 512, either at the start or continuously during a run. There are no interfering ion peaks from this compound in the mass region of interest. The $Cr(tfa)_3$ will be maintained at a constant temperature, hence constant vapor pressure, in a small container within the source vacuum housing which is connected directly to the ion source. Flow of $Cr(tfa)_3$ at the start of a run will either be controlled by an externally switched valve, or the compound will be allowed to flow continuously. Knowledge of absolute signal intensities of the bacterial decomposition products will allow relating peak intensities in various organisms.

It is desired to generate a reference data library of known decomposition curves having minimal errors of reproducibility since it is those reproducibility errors which set the ultimate limit for resolving one organism or specimen from another. Reproducibility of the analytical data may be determined by calculating linear correlation coefficients, $r$, on single ion time dependent curves as shown in FIG. 1F. This calculation may be performed for six to ten ions in every run of each bacterial strain, and will be done by comparing the individual run to the average of previous runs for that ion in the particular strain. The preliminary data have shown that values of $r$ greater than 0.96 are attainable for the experimental data from a limited number of runs. The question of retaining or discarding replicate runs on the basis of agreement with previous runs may be determined by using the value of the linear correlation coefficient of a particular run and the average of previous runs. It is expected that the limits for rejecting replicates having a substantial deviation from a mean value of $r$ will be narrow, but the anticipated breadth of the limits is very dependent on the number of replications performed. For a mean value of $r = 0.96$, determined from 20 replicates, a single determination of $r < 0.90$ may be rejected at the 95% confidence level. If, however, the mean value of $r = 0.97$, only 13 replications have been made, then a single determination of $r < 0.90$ may be rejected at the 95% confidence level. Mean values of $r$ in the region of 0.96–0.97 may be established and the lower limit of standard error set to be no lower than 0.90, therefore indicating thirteen to twenty replicates of each data run on each bacterial strain to produce suitable reference library data.

Analysis of the data generated by the method may proceed in two steps. First, the data may be searched a priori for features which appear to be characteristic. These characteristic features should emerge from a search based on finding peaks of a particular shape at a number of different temperatures and masses as predicted by a preliminary model for the thermal decomposition of cellular material. This method will be based on finding values for the integral of ion intensity vs. time within a particular range of values. It will develop characteristics in terms of location and breadth of the evolution peaks at a particular mass number. If this approach fails to yield a usable quantity of characteristics, then an empirical method similar to that one used for visually judging the data will be used.

After the various features in the data have been found, then they will be classified so that all characteristics belonging to organisms or specimen will be grouped together, and so on for all of the organisms or specimen. Degree of overlap and reliability of separation may be estimated between the various sets of characteristics.

This invention has also been carried out with respect to a preliminary universe of four different types of lymphocytes. Some of the resulting recorded data is set forth in FIGS. 34–42. In particular, the total ion current as a function of time or temperature for two different types of normal lymphocytes are set out in FIGS. 34 and 36 with a representative sample of the mass spectra respectively corresponding thereto set out in FIGS. 35 and 37. Similar total ion plots and representative spectra for lymphocytes known to have chronic lymphocytic leukemia are similarly set forth in FIGS. 38–41. The resulting single ion plots for mass number 411 is set forth in FIG. 42 as a function of time or temperature for each of these four different types of lymphocytes.

It is to be noted that all of the total ion plots for these lymphocytes are more similar to each other than to any of the bacteria and that the two normals are different than the two CLL examples (breadth of main peaks and magnitude of peaks at low scan numbers). Note that the ratio of areas at high and low scan numbers in FIG. 42 is about the same for the two normals, but that the two abnormal cancerous examples are different from the normals and from each other. It turns out that the white cell count of the normals is about 5000/cc, while that of Dokich is ~20,000 and that of Mourfield is ~100,000. The area of m/e 411 ion at high and low scans seems to correlate to this cell count.

Although only a few exemplary embodiments of this invention have been described in detail above, those skilled in the art will recognize that the method described is one which will greatly facilitate the classification and/or identification of biological specimen representative of living tissue. In particular, the method described will greatly facilitate the classification and/or identification of biological organisms such as bacteria, yeast, molds, fungi, viruses and unicellular animals as well as biological tissues such as lymphocytes, leucocytes, phagocytes, erythrocytes and platelets. As will be appreciated, various modifications and/or variations may be made in the exemplary embodiments as described above without materially departing from the novel and advantageous aspects of the invention. Accordingly, all such modifications and variations are intended to be included within the scope of the following appended claims.

What is claimed is:

1. A method facilitating the classification and identification of an unknown biological specimen, said method comprising the following steps:
    (a) providing a physical sample of at least one biological specimen;
    (b) controllably heating said sample in accordance with a predetermined non-isothermal time dependent function so as to cause the sample temperature to increase from a first predetermined temperature to a second higher predetermined temperature during a correspondingly predetermined time span thereby causing the sample to undergo controlled thermal degradation and to give off a characteristic time dependent sequence of gaseous degradation components;
    (c) providing a mass spectrometer having an ionization source therein;
    (d) directly passing said gaseous degradation components within said ionization source from said heating step and ionizing said components in the same characteristic time dependent sequence involved in the formation of said components during said heating step to provide a respectively corresponding time dependent sequence of ions of said components; and
    (e) analyzing and detecting the mass of at least some of said ions of the components within said mass spectrometer during said predetermined time span and recording a set of measured data representing the respective quantities of ions having particular masses being produced as a function of time or temperature during said predetermined time span;
    (f) said steps $a-e$ above being carried out at least once for a sample of biological specimen having known predetermined identity;
    (g) said steps $a-e$ above being repeated at least once for a sample of biological specimen having unknown identity thereby facilitating the classification and identification of such unknown biological specimen through comparison of the set of measured data resulting therefrom with the set of measured data resulting from said steps $a-f$.

2. A method as in claim 1, wherein step $b$ comprises substantially linearly raising the temperature of the sample during said predetermined time span.

3. A method as in claim 1, further comprising the step of repeating steps $a-f$ for a plurality of different biological specimen each having known predetermined identities thereby providing a corresponding plurality of sets of said measured data for comparison with the set of measured data resulting from step $g$.

4. A method as in claim 3, further comprising the steps of:
    cross-correlating the set of measured data resulting from step $g$ with the sets of measured data resulting from repeating steps $a-f$; and
    selecting the set of measured data resulting from repeating steps $a-f$ which most closely correlates with the set of data resulting from step $g$ and classifying and/or identifying the unknown biological specimen based upon the classification and/or identification of the known biological specimen corresponding to said selected set of data.

5. A method as in claim 1, wherein step $d$ comprises ionizing said components in an ionizing process which does not diminish the mass of said components by more than one mass number.

6. A method as in claim 5, wherein said ionizing step comprises chemical ionization of said components.

7. A method as in claim 6, wherein said steps $a$ and $b$ are carried out in a chemical ionization ion source.

8. A method as in claim 7, wherein said step $d$ comprises the passing of a reagent gas over said sample and into a chemical ionization zone within said chemical ionization source whereby said components of thermal degradation are swept along by said reagent gas away from the site of said sample.

9. A method as in claim 1, wherein said steps $a$ and $b$ are carried out within said ionization source.

10. A method as in claim 1, wherein said steps $a$ and $b$ comprise placement of said sample onto a heated solids probe operatively associated with said ionization source.

11. A method as in claim 10, wherein said heated solids probe includes an electrical heater therein for heating said sample and a temperature sensor providing an electrical indication of the probe temperature and including the step of:
    utilizing the temperature sensor electrical output to control the supply of electrical energy to said heater so as to cause the temperature of said sample to increase in accordance with said predetermined non-isothermal time dependent function from said first temperature to said second higher temperature during said corresponding predetermined time span.

12. A method as in claim 1, further comprising the step of:
    detecting the total ion current within said mass spectrometer resulting from the ionization of said components during said predetermined time span and recording further measured data showing the intensity of such total ion current as a function of time or temperature during said predetermined time span;
    said just stated step of detecting the total ion current being included in step $e$ as carried forth in steps $f$ and $g$ to thereby provide said further measured data as a part of the sets of measured data resulting from steps $f$ and $g$.

13. A method as in claim 12, further comprising the step of repeating steps $a-f$ for a plurality of different biological specimen each having known predetermined identities thereby providing a corresponding plurality of sets of said measured data for comparison with the set of measured data resulting from step $g$.

14. A method as in claim 13, further comprising the steps of:
    cross-correlating the set of measured data resulting from step $g$ with the sets of measured data resulting from repeating steps $a-f$; and
    selecting the set of measured data resulting from repeating steps $a-f$ which most closely correlates with the set of data from step $g$ and classifying and/or identifying the unknown bioligical specimen as being of the same classification and/or identification as the known biological specimen corresponding to said selected set of data.

15. A method as in claim 1, further comprising the step of:
   analyzing and detecting the mass of at least some of said ions of the components within said mass spectrometer during said predetermined time span and recording further measured data showing the spectrum and relative quantities of masses comprising said ions at different instants during said predetermined time span; and
   utilizing particular predetermined masses in step e selected from among at least one of the said recorded spectra of masses occurring at some instant during said predetermined time span.

16. A method as in claim 15, wherein the further measured data comprising said spectra of masses is included with the sets of measured data resulting from steps f and g to thereby provide further measured data for use in comparison to classify and/or identify the unknown biological specimen.

17. A method as in claim 16, further comprising the step of repeating steps a–f for a plurality of different biological specimen each having known predetermined identities thereby providing a corresponding plurality of sets of said measured data for comparison with the set of measured data resulting from step g.

18. A method as in claim 17, further comprising the steps of:
   cross-correlating the set of measured data resulting from g with the sets of measured data resulting from repeating steps a–f; and
   selecting the set of measured data resulting from repeating steps a–f which most closely correlates with the set of data resulting from step g and classifying and/or identifying the unknown biological specimen based upon the classification and/or identification of the known biological specimen corresponding to said selected set of data.

19. A method as in claim 15, further comprising the steps of:
   detecting the total ion current within said mass spectrometer resulting from the ionization of said components during said predetermined time span and recording further measured data showing the intensity of such total ion current as a function of time or temperature during said predetermined time span; and
   determining from said total ion current data particular different instants of time during said predetermined time span for recording and utilization of said spectra of masses.

20. A method as in claim 1, wherein said biological specimen includes a biological organism selected from a group comprising bacteria, yeast, molds, fungi, viruses and unicellular animals.

21. A method as in claim 1, wherein said biological specimen includes a biological tissue selected from a group comprising lymphocytes, leucocytes, phagocytes, erythrocytes and platelets.

22. A method facilitating the classification and identifcation of an unknown biological specimen, said method comprising the following steps:
   (a) providing a physical sample of at least one biological specimen;
   (b) controllably heting said sample in accordance with a predetermined non-isothermal time dependent function so as to cause the sample temperature to increase from a first predetermined temperature to a second higher predetermined temperature during a correspondingly predetermined time span thereby causing the sample to undergo controlled thermal degradation and to give off a characteristic time dependent sequence of gaseous degradation components;
   (c) providing a mass spectrometer having a chemical ionization source therein;
   (d) directly passing said gaseous degradation components within said chemical ionization source from said heating step and chemically ionizing said components in the same characteristic time dependent sequence involved in the formation of said components during said heating step to provide a respectively corresponding sequence of chemically ionized ions of said components; and
   (e) analyzing and detecting the intensity of ion current corresponding to different masses of said chemically ionized ions within said mass spectrometer at successive instants of time during said predetermined time span and recording measured data showing the spectrum of ions being produced and their relative intensities at each of said successive instants of time thereby effectively accumulating a three dimensional array of recorded measured data having one functional coordinate corresponding to ion intensity, another functional coordinate corresponding to ion mass and another functional coordinate corresponding to temperature or time elapsed during said predetermined time span;
   (f) said steps a–e above being carried out at least once for a sample of biological specimen having known predetermined identity;
   (g) said steps a–e above being repeated at least once for a sample of biological specimen having unknown identity thereby facilitating the classification and/or identification of such unknown biological specimen through comparison of at least a part of the three dimensional array of measured data resulting therefrom with at least a part of the three dimensional array of measured data resulting from said steps a–f.

23. A method as in claim 22, wherein step b comprises substantially linearly raising the temperature of the sample during said predetermined time span.

24. A method as in claim 22, further comprising the step of repeating steps a–f for a plurality of different biological specimen each having known predetermined identities thereby providing a corresponding plurality of arrays of said measured data for comparison with the array of measured data resulting from step g.

25. A method as in claim 24, further comprising the steps of:
   cross-correlating the array of measured data resulting from step g with the arrays of measured data resulting from repeating steps a–f; and
   selecting the array of measured data resulting from repeating steps a–f which most closely correlates with the array of data resulting from step g and classifying and identifying the unknown biological specimen based upon the classification and identification of the known biological specimen corresponding to said selected array of data.

26. A method as in claim 22, wherein step d comprises ionizing said components in an ionizing process which does not diminish the mass of said components by more than one mass chamber.

27. A method as in claim 26, wherein said ionizing step comprises chemical ionization of said components.

28. A method as in claim 27, wherein said steps $a$ and $b$ are carried out in a chemical ionization ion source.

29. A method as in claim 28, wherein said step $d$ comprises the passing of a reagent gas over said sample and into a chemical ionization zone within said chemical ionization source whereby said components of thermal degradation are swept along by said reagent gas away from the site of said sample.

30. A method as in claim 22, wherein said steps $a$ and $b$ are carried out within said ionization source.

31. A method as in claim 22, wherein said steps $a$ and $b$ comprise placement of said sample onto a heated solids probe operatively associated with said ionization source.

32. A method as in claim 31, wherein said heated solids probe includes an electrical heater therein for heating said sample and a temperature sensor providing an electrical indication of the probe temperature and including the step of:
  utilizing the temperature sensor electrical output to control the supply of electrical energy to said heater so as to cause the temperature of said sample to increase in accordance with said predetermined non-isothermal time dependent function from said first temperature to said second higher temperature during said corresponding predetermined time span.

33. A method as in claim 22, further comprising the step of:
  detecting the total ion current within said mass spectrometer resulting from the ionization of said components during said predetermined time span and recording further measured data showing the intensity of such total ion current as a function of time or temperature during said predetermined time span;
  said just stated step of detecting the total ion current being included in step $e$ as carried forth in steps $f$ and $g$ to thereby provide said further measured data as a part of the arrays of measured data resulting from steps $f$ and $g$.

34. A method as in claim 33, further comprising the step of repeatng steps $a$–$f$ for a plurality of different biological specimen each having known predetermined identities thereby providing a corresponding plurality of arrays of said measured data for comparison with the array of measured data resulting from step $g$.

35. A method as in claim 34, further comprising the steps of:
  cross-correlating the array of measured data resulting from step $g$ with the arrays of measured data resulting from repeating steps $a$–$f$; and
  selecting the array of measured data resulting from repeating steps $a$–$f$ which most closely correlates with the array of data resulting from step $g$ and classifying and/or identifying the unknown biological specimen as being of the same classification and identification as the known biological specimen corresponding to said selected array of data.

36. A method as in claim 22, further comprising the step of:
  analyzing and detecting the mass of at least some of said ions of the components within said mass spectrometer during said predetermined time span and recording further measured data showing the spectrum and relative quantities of masses comprising said ions at different instants during said predetermined time span; and
  utilizing particular predetermined masses in step $e$ from among at least one of the said spectra of masses occurring at some instant during said predetermined time span.

37. A method as in claim 36, wherein the further measured data comprising said spectra of masses is included with the arrays of measured data resulting from steps $f$ and $g$ to thereby provide further measured data for use in comparison to classify and/or identify the unknown biological specimen.

38. A method as in claim 37, further comprising the step of repeating steps $a$–$f$ for a plurality of different biological specimen each having known predetermined identities thereby providing a corresponding plurality of arrays of said measured data for comparison with the array of measured data resulting from step $g$.

39. A method as in claim 38, further comprising the steps of:
  cross-correlating the array of measured data resulting from step $g$ with the arrays of measured data resulting from repeating steps $a$–$f$; and
  selecting the array of measured data resulting from repeating steps $a$–$f$ which most closely correlates with the array of data resulting from step $g$ and classifying and/or identifying the unknown biological specimen based upon the classification and/or identification of the known biological specimen corresponding to said selected array of data.

40. A method as in claim 36, further comprising the steps of:
  detecting the total ion current within said mass spectrometer resulting from the ionization of said components during said predetermined time span and recording further measured data showing the intensity of such total ion current as a function of time or temperature during said predetermined time span; and
  determining from said total ion current data particular different instants of time during said predetermined time span for recording and utilization of said spectra of masses.

41. A method as in claim 22, wherein said biological specimen includes a biological organism selected from a group comprising bacteria, yeast, molds, fungi, viruses and unicellular animals.

42. A method as in claim 22, wherein said biological specimen includes a biological tissue selected from a group comprising lymphocytes, leucocytes, phagocytes, erythrocytes and platelets.

43. A method facilitating the classification and identification of an unknown biological specimen, said method comprising the following steps:
  (a) providing a physical sample of a biological specimen;
  (b) controllably heating said sample in accordance with a predetermined non-isothermal time dependent function so as to cause the sample temperature to increase from a first predetermined temperature to a second higher predetermined temperature during a correspondingly predetermined time span thereby causing the sample to undergo controlled thermal degradation and to give off a characteristic time dependent sequence of gaseous degradation components;
  (c) providing a mass spectrometer having an ionization source therein:
  (d) directly passing said gaseous degradation components within said ionization source from said heating step and ionizing said components in the same characteristic time dependent sequence involved in the formation of said components during said heating step to provide a respectively corresponding time dependent sequence of ions of said components; and (e) analyzing and detecting the mass of at least some of said ions of the components within said mass spectrometer during said predetermined time span and recording a set of measured data representing the respective quantities of ions having particular masses being produced as a function of time or temperature during said predetermined time span thereby facilitating the classification and identification of the specimen through comparison of the resulting set of recorded measured data with other sets of previously recorded measured data produced by carrying out the above steps $a$–$e$ for biological specimen having known identification or classification.

44. A method as in claim 43, wherein step $b$ comprises substantially linearly raising the temperature of the sample during said predetermined time span.

45. A method as in claim 43, wherein step $d$ comprises ionizing said components in an ionizing process which does not diminish the mass of said components by more than one mass number.

46. A method as in claim 45, wherein said ionizing step comprises chemical ionization of said components.

47. A method as in claim 46, wherein said steps $a$ and $b$ are carried out in a chemical ionization ion source.

48. A method as in claim 47, wherein said step $d$ comprises the passing of a reagent gas over said sample and into a chemical ionization zone within said chemical ionization source whereby said components of thermal degradation are swept along by said reagent gas away from the site of said sample.

49. A method as in claim 43, wherein said steps $a$ and $b$ are carried out within said ionization source.

50. A method as in claim 43, wherein said steps $a$ and $b$ comprise placement of said sample onto a heated solids probe operatively associated with said ionization source.

51. A method as in claim 50, wherein said heated solids probe includes an electrical heater therein for heating said sample and a temperature sensor providing an electrical indication of the probe temperature and including the step of:

utilizing the temperature sensor electrical output to control the supply of electrical energy to said heater so as to cause the temperature of said sample to increase in accordance with said predetermined non-isothermal time dependent function from said first temperature to said second higher temperature during said corresponding predetermined time span.

52. A method as in claim 43, further comprising the step of:

detecting the total ion current within said mass spectrometer resulting from the ionization of said components during said predetermined time span and recording further measured data showing the intensity of such total ion current as a function of the time or temperature during said predetermined time span;

said just stated step of detecting the total ion current being included in step $e$ to thereby provide said further measured data as a part of the recorded measured data.

53. A method as in claim 43, further comprising the step of:

analyzing and detecting the mass of at least some of said ions of the components within mass spectrometer during said predetermined time span and recording further measured data showing the spectrum and relative quantities of masses comprising said ions at different instants during said predetermined time span; and utilizing particular predetermined masses in step $e$ selected from among at least one of the said recorded spectra of masses occurring at some instant during said predetermined time span.

54. A method as in claim 53, further comprising the steps of:

detecting the total ion current within said mass spectrometer resulting from the ionization of said components during said predetermined time span and recording further measured data showing the intensity of such total ion current as a function of time or temperature during said predetermined time span; and determining from said total ion current data particular different instants of time during said predetermined time span for recording and utilization of said spectra of masses.

55. A method as in claim 43, wherein said biological specimen includes a biological organism selected from a group comprising bacterial, yeast, molds, fungi, viruses and unicellular animals.

56. A method in claim 43, wherein said biological specimen includes a biological tissue selected from a group comprising lymphocytes, leucocytes, phagocytes, erythrocytes and platelets.

* * * * *